US012054729B2

(12) United States Patent
Daum et al.

(10) Patent No.: US 12,054,729 B2
(45) Date of Patent: Aug. 6, 2024

(54) USE OF CRY14 FOR THE CONTROL OF NEMATODE PESTS

(71) Applicant: BASF Agricultural Solutions Seed US LLC, Florham Park, NJ (US)

(72) Inventors: Julia Daum, Apex, NC (US); Axel Elling, Cary, NC (US)

(73) Assignee: BASF Agricultural Solutions Seed US LLC, Florham Park, NJ (US)

( * ) Notice: Subject to any disclaimer, the term of this patent is extended or adjusted under 35 U.S.C. 154(b) by 0 days.

(21) Appl. No.: 17/214,022

(22) Filed: Mar. 26, 2021

(65) Prior Publication Data

US 2021/0212323 A1 Jul. 15, 2021

Related U.S. Application Data

(63) Continuation of application No. 16/468,569, filed as application No. PCT/US2017/068070 on Dec. 22, 2017, now abandoned.

(60) Provisional application No. 62/438,420, filed on Dec. 22, 2016.

(51) Int. Cl.
*C12N 15/82* (2006.01)

(52) U.S. Cl.
CPC ..... *C12N 15/8285* (2013.01); *C12N 15/8286* (2013.01)

(58) Field of Classification Search
CPC .................................................. C12N 15/8285
See application file for complete search history.

(56) References Cited

U.S. PATENT DOCUMENTS

2007/0294787 A1* 12/2007 Carozzi .............. C12N 15/8286 536/23.6
2010/0024075 A1* 1/2010 Aroian ................. C07K 14/325 800/301
2015/0274786 A1* 10/2015 Bowen ................... A01N 63/50 514/4.5
2016/0066584 A9 3/2016 Jackson et al.

FOREIGN PATENT DOCUMENTS

CN 101501066 A 8/2009
EP 0462721 B1 12/1991
WO WO1993019604 A1 10/1993
WO WO1994016079 A2 7/1994
WO WO2007147029 A2 12/2007
WO WO2010027808 A2 3/2010

OTHER PUBLICATIONS

Grossi-de-Sa et al (Chapter 19. Genetically Modified Soybean for Insect-Pests and Disease Control, 429-452, 2011) (Year: 2011).*
Crow (Amaryllis Lesion Nematode, *Pratylenchus hippeastri* Inserra et al., 2006 (Nematoda: Tylenchida: Pratylenchidae). Univercity of Florida IFAS Extension. p. 1-4, 2006). (Year: 2006).*
Berlitz et al (Bacillus and Biopesticides in Control of Phytonematodes. Chapter 1, 3-16, 2014) (Year: 2014).*
Jones et al (Molecular biology of root lesion nematodes (*Pratylenchus* spp.) and their interaction with host plants. Annals of Applied Biology. 164, p. 163-181, 2014). (Year: 2014).*
International Search Report for PCT Patent Application No. PCT/US2017/068070, Issued on May 17, 2018, 7 pages.
International Preliminary Report on Patentability for PCT Patent Application No. PCT/US2017/068070, Issued on Jun. 25, 2019, 8 pages.
Written Opinion of the International Searching Authority for PCT Patent Application No. PCT/US2017/068070, Issued on Jun. 28, 2018, 7 pages.
Aronson, A. and Shai, Y., "Why Bacillus thuringiensis insecticidal toxins are so ejective: unique features of their mode of action," FEMS Microbiology Letters 195 (2001) pp. 1-8.
Atkinson et al., "Engineering Plants for Nematode Resistance," Annu. Rev. Phytopathol, 2003, 41, pp. 615-639.
De Maagd et al., "Identification of Bacillus thuringiensis Delta-Endotoxin Cry1C Domain III Amino Acid Residues Involved in Insect Specificity," Applied and Environmental Microbiology, Oct. 1999, pp. 4369-4374.
De Maagd et al., "How Bacillus thuringiensis has evolved specific toxins to colonize the insect world," TRENDS in Genetics, vol. 17 No. 4, Apr. 2001, pp. 193-199.
Li et al., "Resistance to root-knot nematode in tomato roots expressing a nematicidal Bacillus thuringiensis crystal protein," Plant Biotechnology Journal (2007) vol. 5 , pp. 455-464.
Saraswathy, N. and Kumar, P., "Protein engineering of o-endotoxins of Bacillus thuringiensis," Electronic Journal of Biotechnology, vol. 7 No. 2, Issue of Aug. 15, 2004, pp. 178-188.
Tounsi et al., "Cloning and study of the expression of a novel cry1la-type gene from *Bacillus thuringiensis* subsp. kurstaki," Journal of Applied Microbiology, 2003, vol. 95, pp. 23-28.
Wei et al., "Bacillus thuringiensis crystal proteins that target nematodes," PNAS, 2003, vol. 100, No. 5, pp. 2760-2765.

* cited by examiner

*Primary Examiner* — Charles Logsdon
*Assistant Examiner* — Wayne Zhong
(74) *Attorney, Agent, or Firm* — BASF Corporation

(57) ABSTRACT

Compositions and methods for conferring nematicidal activity to bacteria, plants, plant cells, tissues and seeds are provided. In particular, methods for killing or controlling a nematode pest population, particularly a *Pratylenchus* spp., e.g., *Pratylenchus brachyurus*, root knot nematode, reniform nematode, or Lance nematode population, are provided. The methods include contacting the nematode pest with a pesticidally-effective amount of a polypeptide comprising a nematicidal toxin, particularly a nematicidal toxin active against a *Pratylenchus* spp. nematode, e.g. *Pratylenchus brachyurus*. Further included are methods for increasing yield in plants by expressing the toxin of the invention.

5 Claims, 2 Drawing Sheets

Specification includes a Sequence Listing.

SEQUENCE LISTING

```
<160> NUMBER OF SEQ ID NOS: 7

<210> SEQ ID NO 1
<211> LENGTH: 1186
<212> TYPE: PRT
<213> ORGANISM: Bacillus thuringiensis

<400> SEQUENCE: 1

Met Asp Cys Asn Leu Gln Ser Gln Gln Asn Ile Pro Tyr Asn Val Leu
1               5                   10                  15

Ala Ile Pro Val Ser Asn Val Asn Ala Leu Val Asp Thr Ala Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Ala Phe Asn
    50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Val Asn Met Val Ile Gly Trp
                85                  90                  95

Leu Trp Pro His Lys Asn Lys Thr Ala Asp Thr Glu Asn Leu Ile Lys
            100                 105                 110

Leu Ile Asp Glu Glu Ile Gln Lys Gln Leu Asn Lys Ala Leu Leu Asp
        115                 120                 125

Gln Asp Arg Asn Asn Trp Thr Ser Phe Leu Glu Ser Ile Phe Asp Thr
```

```
    130                 135                 140

Ser Ala Thr Val Ser Asn Ala Ile Ile Asp Ala Gln Trp Ser Gly Thr
145                 150                 155                 160

Val Asp Thr Thr Asn Arg Gln Gln Lys Thr Pro Thr Thr Ser Asp Tyr
                165                 170                 175

Leu Asn Val Val Gly Lys Phe Asp Ser Ala Asp Ser Ser Ile Ile Thr
            180                 185                 190

Asn Glu Asn Gln Ile Met Asn Gly Asn Phe Asp Val Ala Ala Ala Pro
        195                 200                 205

Tyr Phe Val Ile Gly Ala Thr Leu Arg Leu Ser Leu Tyr Gln Ser Tyr
    210                 215                 220

Ile Lys Phe Cys Asn Ser Trp Ile Asp Ala Val Gly Phe Ser Thr Asn
225                 230                 235                 240

Asp Ala Asn Thr Gln Lys Ala Asn Leu Ala Arg Thr Lys Leu Thr Met
                245                 250                 255

Arg Thr Thr Ile Asn Glu Tyr Thr Gln Arg Val Met Lys Val Phe Lys
            260                 265                 270

Asp Ser Lys Asn Met Pro Thr Ile Gly Thr Asn Lys Phe Ser Val Asp
        275                 280                 285

Ala Tyr Asn Val Tyr Val Lys Gly Met Thr Leu Asn Val Leu Asp Met
    290                 295                 300

Val Ala Ile Trp Ser Ser Leu Tyr Pro Asn Asp Tyr Thr Ser Gln Thr
305                 310                 315                 320

Ala Ile Glu Gln Thr Arg Val Thr Phe Ser Asn Met Val Gly Gln Glu
                325                 330                 335

Glu Gly Thr Asp Gly Thr Leu Lys Ile Tyr Asn Thr Phe Asp Ser Leu
            340                 345                 350

Ser Tyr Gln His Ser Leu Ile Pro Asn Asn Asn Val Asn Leu Ile Ser
        355                 360                 365

Tyr Tyr Thr Asp Glu Leu Gln Asn Leu Glu Leu Ala Val Tyr Thr Pro
    370                 375                 380

Lys Gly Gly Ser Gly Tyr Ala Tyr Pro Tyr Gly Phe Ile Leu Asn Tyr
385                 390                 395                 400

Ala Asn Ser Asn Tyr Lys Tyr Gly Asp Asn Asp Pro Thr Gly Lys Pro
                405                 410                 415

Leu Asn Lys Gln Asp Gly Pro Ile Gln Gln Ile Asn Ala Ala Thr Gln
            420                 425                 430

Asn Ser Lys Tyr Leu Asp Gly Glu Thr Ile Asn Gly Ile Gly Ala Ser
        435                 440                 445

Leu Pro Gly Tyr Cys Thr Thr Gly Cys Ser Ala Thr Glu Gln Pro Phe
    450                 455                 460

Ser Cys Thr Ser Thr Ala Asn Ser Tyr Lys Ala Ser Cys Asn Pro Ser
465                 470                 475                 480

Asp Thr Asn Gln Lys Ile Asn Ala Leu Tyr Ala Phe Thr Gln Thr Asn
                485                 490                 495

Val Lys Gly Ser Thr Gly Lys Leu Gly Val Leu Ala Ser Leu Val Pro
            500                 505                 510

Tyr Asp Leu Asn Pro Lys Asn Val Phe Gly Glu Leu Asp Ser Asp Thr
        515                 520                 525

Asn Asn Val Ile Leu Lys Gly Ile Pro Ala Glu Lys Gly Tyr Phe Pro
    530                 535                 540

Asn Asn Ala Arg Pro Thr Val Val Lys Glu Trp Ile Asn Gly Ala Ser
545                 550                 555                 560
```

```
Ala Val Pro Phe Tyr Ser Gly Asn Thr Leu Phe Met Thr Ala Thr Asn
                565                 570                 575

Leu Thr Ala Thr Gln Tyr Lys Ile Arg Ile Arg Tyr Ala Asn Pro Asn
            580                 585                 590

Ser Asp Thr Gln Ile Gly Val Leu Ile Thr Gln Asn Gly Ser Gln Ile
        595                 600                 605

Ser Asn Ser Asn Leu Thr Leu Tyr Ser Thr Thr Asp Ser Ser Met Ser
    610                 615                 620

Ser Asn Leu Pro Gln Asn Val Tyr Val Thr Gly Glu Asn Gly Asn Tyr
625                 630                 635                 640

Thr Leu Leu Asp Leu Tyr Ser Thr Thr Asn Val Leu Ser Thr Gly Asp
                645                 650                 655

Ile Thr Leu Lys Leu Thr Gly Gly Asn Gln Lys Ile Phe Ile Asp Arg
            660                 665                 670

Ile Glu Phe Ile Pro Thr Met Pro Val Pro Ala Pro Thr Asn Asn Thr
        675                 680                 685

Asn Asn Asn Asn Gly Asp Asn Gly Asn Asn Asn Pro Pro His His Gly
    690                 695                 700

Cys Ala Ile Ala Gly Thr Gln Gln Leu Cys Ser Gly Pro Pro Lys Phe
705                 710                 715                 720

Glu Gln Val Ser Asp Leu Glu Lys Ile Thr Thr Gln Val Tyr Met Leu
                725                 730                 735

Phe Lys Ser Ser Ser Tyr Glu Glu Leu Ala Leu Lys Val Ser Ser Tyr
            740                 745                 750

Gln Ile Asn Gln Val Ala Leu Lys Val Met Ala Leu Ser Asp Glu Lys
        755                 760                 765

Phe Cys Glu Glu Lys Arg Leu Leu Arg Lys Leu Val Asn Lys Ala Asn
    770                 775                 780

Gln Leu Leu Glu Ala Arg Asn Leu Leu Val Gly Gly Asn Phe Glu Thr
785                 790                 795                 800

Thr Gln Asn Trp Val Leu Gly Thr Asn Ala Tyr Ile Asn Tyr Asp Ser
                805                 810                 815

Phe Leu Phe Asn Gly Asn Tyr Leu Ser Leu Gln Pro Ala Ser Gly Phe
            820                 825                 830

Phe Thr Ser Tyr Ala Tyr Gln Lys Ile Asp Glu Ser Thr Leu Lys Pro
        835                 840                 845

Tyr Thr Arg Tyr Lys Val Ser Gly Phe Ile Gly Gln Ser Asn Gln Val
    850                 855                 860

Glu Leu Ile Ile Ser Arg Tyr Gly Lys Glu Ile Asp Lys Ile Leu Asn
865                 870                 875                 880

Val Pro Tyr Ala Gly Pro Leu Pro Ile Thr Ala Asp Ala Ser Ile Thr
                885                 890                 895

Cys Cys Ala Pro Glu Ile Asp Gln Cys Asp Gly Gly Gln Ser Asp Ser
            900                 905                 910

His Phe Phe Asn Tyr Ser Ile Asp Val Gly Ala Leu His Pro Glu Leu
        915                 920                 925

Asn Pro Gly Ile Glu Ile Gly Leu Lys Ile Val Gln Ser Asn Gly Tyr
    930                 935                 940

Ile Thr Ile Ser Asn Leu Glu Ile Ile Glu Glu Arg Pro Leu Thr Glu
945                 950                 955                 960

Met Glu Ile Gln Ala Val Asn Arg Lys Asp Gln Lys Trp Lys Arg Glu
                965                 970                 975
```

```
Lys Leu Leu Glu Cys Ala Ser Val Ser Glu Leu Leu Gln Pro Ile Ile
            980                 985                 990

Asn Gln Ile Asp Ser Leu Phe Lys  Asp Ala Asn Trp Tyr  Asn Asp Ile
        995                 1000                1005

Leu Pro  His Val Thr Tyr Gln  Thr Leu Lys Asn Ile  Ile Val Pro
    1010                 1015                1020

Asp Leu  Pro Lys Leu Lys His  Trp Phe Ile Asp His  Leu Pro Gly
    1025                 1030                1035

Glu Tyr  His Glu Ile Glu Gln  Lys Met Lys Glu Ala  Leu Lys His
    1040                 1045                1050

Ala Phe  Thr Gln Leu Asp Glu  Lys Asn Leu Ile His  Asn Gly His
    1055                 1060                1065

Phe Ala  Thr Asn Leu Ile Asp  Trp Gln Val Glu Gly  Asp Ala Arg
    1070                 1075                1080

Met Lys  Val Leu Glu Asn Asp  Ala Leu Ala Leu Gln  Leu Ser Asn
    1085                 1090                1095

Trp Asp  Ser Ser Val Ser Gln  Ser Ile Asp Ile Leu  Glu Phe Asp
    1100                 1105                1110

Glu Asp  Lys Ala Tyr Lys Leu  Arg Val Tyr Ala Gln  Gly Ser Gly
    1115                 1120                1125

Thr Ile  Gln Phe Gly Asn Cys  Glu Asp Glu Ala Ile  Gln Phe Asn
    1130                 1135                1140

Thr Asn  Ser Phe Val Tyr Lys  Glu Lys Ile Ile Tyr  Phe Asp Thr
    1145                 1150                1155

Pro Ser  Ile Asn Leu His Ile  Gln Ser Glu Gly Ser  Glu Phe Val
    1160                 1165                1170

Val Ser  Ser Ile Asp Leu Val  Glu Leu Ser Asp Asp  Glu
    1175                 1180                1185


<210> SEQ ID NO 2
<211> LENGTH: 1185
<212> TYPE: PRT
<213> ORGANISM: Bacillus thuringiensis

<400> SEQUENCE: 2

Met Asp Cys Asn Leu Gln Ser Gln Gln Asn Ile Pro Tyr Asn Val Leu
1               5                   10                  15

Ala Ile Pro Val Ser Asn Val Asn Ser Leu Thr Asp Thr Val Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Thr Phe Asn
    50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Ile Asn Met Val Ile Gly Trp
                85                  90                  95

Leu Trp Pro His Lys Asn Lys Asn Ala Asp Thr Glu Asn Leu Ile Asn
            100                 105                 110

Leu Ile Asp Ser Glu Ile Gln Lys Gln Leu Asn Lys Ala Leu Leu Asp
        115                 120                 125

Ala Asp Arg Asn Glu Trp Ser Ser Tyr Leu Glu Ser Ile Phe Asp Ser
    130                 135                 140

Ser Asn Asn Leu Asn Gly Ala Ile Val Asp Ala Gln Trp Ser Gly Thr
145                 150                 155                 160
```

```
Val Asn Thr Thr Asn Arg Thr Leu Arg Asn Pro Thr Glu Ser Asp Tyr
                165                 170                 175

Thr Asn Val Val Thr Asn Phe Ile Ala Ala Asp Gly Asp Ile Ala Asn
            180                 185                 190

Asn Glu Asn His Ile Met Asn Gly Asn Phe Asp Val Ala Ala Ala Pro
        195                 200                 205

Tyr Phe Val Ile Gly Ala Thr Ala Arg Phe Ala Ala Met Gln Ser Tyr
    210                 215                 220

Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
                245                 250                 255

Arg Asn Ala Ile Leu Asn Tyr Thr Gln Gln Val Met Lys Val Phe Lys
            260                 265                 270

Asp Ser Lys Asn Met Pro Thr Ile Gly Thr Asn Lys Phe Ser Val Asp
        275                 280                 285

Thr Tyr Asn Val Tyr Ile Lys Gly Met Thr Leu Asn Val Leu Asp Ile
    290                 295                 300

Val Ala Ile Trp Pro Ser Leu Tyr Pro Asp Asp Tyr Thr Ser Gln Thr
305                 310                 315                 320

Ala Leu Glu Gln Thr Arg Val Thr Phe Ser Asn Met Val Gly Gln Glu
                325                 330                 335

Glu Gly Thr Asp Gly Ser Leu Arg Ile Tyr Asn Thr Phe Asp Ser Phe
            340                 345                 350

Ser Tyr Gln His Ser Pro Ile Pro Asn Asn Asn Val Asn Leu Ile Ser
        355                 360                 365

Tyr Tyr Asn Asp Glu Leu Gln Asn Leu Glu Leu Gly Val Tyr Thr Pro
    370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
                405                 410                 415

Leu Gly Gly Leu Ser Thr Leu Ser Ala Pro Ile Gln Gln Val Asn Ala
            420                 425                 430

Ala Thr Gln Asn Ser Lys Tyr Leu Asp Gly Glu Ile Leu Asn Gly Ile
        435                 440                 445

Gly Ala Ser Leu Pro Gly Tyr Cys Thr Thr Gly Cys Ser Pro Thr Glu
    450                 455                 460

Pro Pro Phe Ser Cys Thr Ser Thr Ala Asn Gly Tyr Lys Ala Ser Cys
465                 470                 475                 480

Asn Pro Ser Asp Thr Asn Gln Lys Ile Asn Ala Leu Tyr Pro Phe Thr
                485                 490                 495

Gln Ala Asn Val Lys Gly Asn Thr Gly Lys Leu Gly Val Leu Ala Ser
            500                 505                 510

Leu Val Ser Tyr Asp Leu Asn Pro Lys Asn Val Phe Gly Glu Leu Asp
        515                 520                 525

Ser Asp Thr Asn Asn Val Ile Leu Lys Gly Ile Pro Ala Glu Lys Gly
    530                 535                 540

Tyr Phe Pro Asn Asn Ala Arg Pro Thr Val Val Lys Glu Trp Ile Asn
545                 550                 555                 560

Gly Ala Ser Ala Val Pro Leu Asp Ser Gly Asn Thr Leu Phe Met Thr
                565                 570                 575
```

```
Ala Thr Asn Leu Thr Ala Thr Gln Tyr Arg Ile Arg Ile Arg Tyr Ala
            580                 585                 590

Asn Pro Asn Ser Asn Thr Gln Ile Gly Val Arg Ile Thr Gln Asn Gly
        595                 600                 605

Ser Leu Ile Ser Ser Ser Asn Leu Thr Leu Tyr Ser Thr Thr Asp Met
    610                 615                 620

Asn Asn Thr Leu Pro Leu Asn Val Tyr Val Ile Gly Glu Asn Gly Asn
625                 630                 635                 640

Tyr Thr Leu Gln Asp Leu Tyr Asn Thr Thr Asn Val Leu Ser Thr Gly
                645                 650                 655

Asp Ile Thr Leu Gln Ile Thr Gly Gly Asp Gln Lys Ile Phe Ile Asp
            660                 665                 670

Arg Ile Glu Phe Val Pro Thr Met Pro Val Pro Gly Asn Thr Asn Asn
        675                 680                 685

Asn Asn Gly Asn Asn Asn Gly Asn Asn Asn Pro Pro His His Val Cys
    690                 695                 700

Ala Ile Ala Gly Thr Gln Gln Ser Cys Ser Gly Pro Pro Lys Phe Glu
705                 710                 715                 720

Gln Val Ser Asp Leu Glu Lys Ile Thr Thr Gln Val Tyr Met Leu Phe
                725                 730                 735

Lys Ser Ser Pro Tyr Glu Glu Leu Ala Leu Glu Val Ser Ser Tyr Gln
            740                 745                 750

Ile Ser Gln Val Ala Leu Lys Val Met Ala Leu Ser Asp Glu Leu Phe
        755                 760                 765

Cys Glu Glu Lys Asn Val Leu Arg Lys Leu Val Asn Lys Ala Lys Gln
    770                 775                 780

Leu Leu Glu Ala Ser Asn Leu Leu Val Gly Gly Asn Phe Glu Thr Thr
785                 790                 795                 800

Gln Asn Trp Val Leu Gly Thr Asn Ala Tyr Ile Asn Tyr Asp Ser Phe
                805                 810                 815

Leu Phe Asn Gly Asn Tyr Leu Ser Leu Gln Pro Ala Ser Gly Phe Phe
            820                 825                 830

Thr Ser Tyr Ala Tyr Gln Lys Ile Asp Glu Ser Thr Leu Lys Pro Tyr
        835                 840                 845

Thr Arg Tyr Lys Val Ser Gly Phe Ile Gly Gln Ser Asn Gln Val Glu
    850                 855                 860

Leu Ile Ile Ser Arg Tyr Gly Lys Glu Ile Asp Lys Ile Leu Asn Val
865                 870                 875                 880

Pro Tyr Ala Gly Pro Leu Pro Ile Thr Ala Asp Ala Ser Ile Thr Cys
                885                 890                 895

Cys Ala Pro Glu Ile Gly Gln Cys Asp Gly Glu Gln Ser Asp Ser His
            900                 905                 910

Phe Phe Asn Tyr Ser Ile Asp Val Gly Ala Leu His Pro Glu Leu Asn
        915                 920                 925

Pro Gly Ile Glu Ile Gly Leu Lys Ile Val Gln Ser Asn Gly Tyr Ile
    930                 935                 940

Thr Ile Ser Asn Leu Glu Ile Ile Glu Glu Arg Pro Leu Thr Glu Met
945                 950                 955                 960

Glu Ile Gln Ala Val Asn Arg Lys Asn Gln Lys Trp Glu Arg Glu Lys
                965                 970                 975

Leu Leu Glu Cys Ala Ser Ile Ser Glu Leu Leu Gln Pro Ile Ile Asn
            980                 985                 990

Gln Ile Asp Ser Leu Phe Lys Asp  Gly Asn Trp Tyr Asn  Asp Ile Leu
```

```
        995                 1000                1005

Pro His  Val Thr Tyr Gln Asp  Leu Lys Asn Ile Ile  Ile Pro Glu
    1010                 1015                1020

Leu Pro  Lys Leu Lys His Trp  Phe Ile Glu Asn Leu  Pro Gly Glu
    1025                 1030                1035

Tyr His  Glu Ile Glu Gln Lys  Met Lys Glu Ala Leu  Lys Tyr Ala
    1040                 1045                1050

Phe Thr  Gln Leu Asp Glu Lys  Asn Leu Ile His Asn  Gly His Phe
    1055                 1060                1065

Thr Thr  Asn Leu Ile Asp Trp  Gln Val Glu Gly Asp  Ala Gln Met
    1070                 1075                1080

Lys Val  Leu Glu Asn Asp Ala  Leu Ala Leu Gln Leu  Phe Asn Trp
    1085                 1090                1095

Asp Ala  Ser Ala Ser Gln Ser  Ile Asn Ile Leu Glu  Phe Asp Glu
    1100                 1105                1110

Asp Lys  Ala Tyr Lys Leu Arg  Val Tyr Ala Gln Gly  Ser Gly Thr
    1115                 1120                1125

Ile Gln  Phe Gly Asn Cys Glu  Asp Glu Ala Ile Gln  Phe Asn Thr
    1130                 1135                1140

Asn Ser  Phe Ile Tyr Gln Glu  Lys Ile Val Tyr Phe  Asp Thr Pro
    1145                 1150                1155

Ser Val  Asn Leu His Ile Gln  Ser Glu Gly Ser Glu  Phe Ile Val
    1160                 1165                1170

Ser Ser  Ile Asp Leu Ile Glu  Leu Ser Asp Asp Gln
    1175                 1180                1185


<210> SEQ ID NO 3
<211> LENGTH: 3561
<212> TYPE: DNA
<213> ORGANISM: Artificial Sequence
<220> FEATURE:
<223> OTHER INFORMATION: Synthetic gene encoding Cry14Aa1

<400> SEQUENCE: 3

atggattgca acctccaaag ccagcagaac attccctaca atgtgctggc cattcctgtt     60

tccaatgtga atgctttggt ggacactgct ggagatttga agaaggcttg ggaggagttc    120

cagaagactg gaagtttctc tctcactgct ctccagcaag gcttctcagc aagccaagga    180

ggagctttta actacttgac cctgctgcaa agtggcatct ctcttgctgg aagttttgtt    240

cctggaggaa cctttgtggc tccaattgtc aacatggtga ttggatggct atggcctcac    300

aagaacaaga ctgctgacac agagaacctc atcaagctga ttgatgaaga gatccagaag    360

cagctgaaca aggctctgct ggatcaagac aggaacaact ggacttcctt cttggagagc    420

atctttgaca cttctgccac tgtttcaaat gccatcattg atgctcaatg gagtggaact    480

gtggacacaa ccaacaggca gcagaagaca ccaacaactt cagattactt gaatgtggtg    540

ggaaagtttg attctgctga ttcttccatc atcaccaatg agaaccagat catgaatggg    600

aactttgatg ttgctgctgc tccatatttt gtgattggag caaccttgag gctctctctc    660

taccaaagct acatcaagtt ctgcaactct tggattgatg ctgttggctt ctcaaccaat    720

gatgccaaca ctcagaaggc aaacttggca aggaccaagc tgacaatgag aaccaccatc    780

aatgagtaca cccagagggt gatgaaggtg ttcaaggatt caaagaacat gccaaccatt    840

ggaaccaaca agttctctgt ggatgcttac aatgtttatg tgaaggggat gactctcaat    900

gtgctggaca tggtggccat ttggagttct ctctatccaa atgattacac aagccaaact    960
```

```
gccattgagc aaacaagggt gaccttctca aacatggtgg gccaagaaga aggaactgat   1020
ggaaccttga agatctacaa cacctttgat tctctctctt atcagcactc tctcatcccc   1080
aacaacaatg tgaacttgat ttcctactac actgatgagc tgcaaaactt ggagctggct   1140
gtttacaccc caaagggagg aagtggctat gcttaccctt atggcttcat cctgaactat   1200
gccaactcaa actacaagta tggagacaat gatccaactg ggaagcctct caacaagcaa   1260
gatgggccaa tccagcagat caatgctgca acccaaaaca gcaaatattt ggatggagaa   1320
accataaatg gcattggagc ttctcttcct ggctattgca ccactggctg ctctgcaaca   1380
gagcagccct tctcttgcac ctcaacagca aacagctaca aggcaagctg caacccttct   1440
gacacaaatc aaaagattaa tgctctctat gccttcaccc aaaccaatgt gaagggaagc   1500
actggaaagc tgggagtgct ggcttccctg gtgccatatg atctcaaccc aaagaatgtg   1560
tttggagagt tggattcaga caccaacaat gtgatcttga aggggattcc tgctgagaag   1620
ggatatttcc ccaacaatgc aaggccaaca gtggtgaagg aatggatcaa tggagcttct   1680
gctgtgccct tctacagtgg caacaccctc ttcatgacag caaccaactt gacagcaacc   1740
caatataaga tcaggatcag atatgccaac ccaaattcag acacccagat tggagtgctg   1800
atcacccaga atgggagcca aatttcaaat tccaacttga ctctctactc aacaactgat   1860
tcttccatgt caagcaacct tcctcagaat gtttatgtca ctggagagaa tgggaactac   1920
accttgctgg atctctattc aacaaccaat gtgctctcaa ctggagacat caccctgaag   1980
ctcactggag gaaaccagaa gatcttcatt gacaggattg agttcatccc aacaatgcca   2040
gttcctgctc caaccaacaa caccaacaac aacaatggag acaatggcaa caacaaccct   2100
cctcaccatg gctgtgccat agctggaacc cagcagcttt gcagtggccc tccaaagttt   2160
gagcaagttt cagatttgga gaagatcacc acccaagttt acatgctctt caagagttca   2220
agctatgaag agcttgctct caaggtttca agctaccaga tcaaccaagt ggctctcaag   2280
gtgatggctc tctctgatga gaagttctgt gaagagaaga ggttattgag gaagctggtg   2340
aacaaggcaa accagctgct ggaagcaagg aacctgctgg ttggaggaaa ctttgaaacc   2400
acccagaatt gggtgcttgg aaccaatgct tacatcaact atgattcctt cctcttcaat   2460
gggaactatc tctccttgca gccagcttct ggcttcttca ccagctatgc ttaccagaag   2520
attgatgaat caaccttgaa gccatacaca agatacaagg tttctggctt cattggccaa   2580
agcaaccaag tggagctgat catctcaaga tatgggaagg agattgacaa gatcctcaat   2640
gtgccatatg ctggccctct tcccatcact gctgatgctt ccatcacttg ctgtgctcca   2700
gagattgatc aatgtgatgg aggccaaagt gattctcact tcttcaacta ttcaattgat   2760
gttggtgctc tccatccaga gctgaaccct ggcattgaga ttggcttgaa gattgtgcaa   2820
agcaatggct acatcaccat cagcaacttg gagatcattg aagagaggcc tctcacagag   2880
atggagatcc aagctgtgaa caggaaggat cagaagtgga agagagagaa gctgctggag   2940
tgtgcttctg tttcagagct gctgcaaccc atcatcaacc agattgattc tctcttcaag   3000
gatgccaatt ggtacaatga cattcttcct catgtgacat accaaacctt gaagaacatc   3060
attgtgccag atcttccaaa gctaaagcat tggttcattg atcaccttcc tggagaatac   3120
catgagattg agcagaagat gaaggaagcc ctgaagcatg ccttcaccca gctggatgag   3180
aagaacttga tccacaatgg ccactttgca accaacttga ttgattggca agtggaagga   3240
gatgcaagga tgaaggtgct ggagaacaat gctttggcct tgcagctctc aaattgggat   3300
```

```
tcttctgttt ctcaatctat tgacatcctg gagtttgatg aagacaaggc ctacaagctg   3360

agggtttatg ctcaaggaag tggaaccatc cagtttggga actgtgaaga tgaagccatc   3420

cagttcaaca ccaacagctt tgtttacaag gagaagatca tctactttga cactccttca   3480

atcaacctcc acatccagag tgaaggaagt gagtttgtgg tttcttccat tgatttggtg   3540

gagctttctg atgatgagta a                                             3561


<210> SEQ ID NO 4
<211> LENGTH: 3558
<212> TYPE: DNA
<213> ORGANISM: Artificial Sequence
<220> FEATURE:
<223> OTHER INFORMATION: Synthetic gene encoding Cry14Ab1

<400> SEQUENCE: 4

atggattgca accttcagtc ccagcagaac attccataca acgtgctcgc tattccagtt     60

tctaacgtga actcccttac tgataccgtg ggtgatctta agaaggcttg ggaagagttc    120

caaaagaccg gatctttctc tcttactgct ctccaacagg gattctctgc ttctcaaggt    180

ggaaccttca actaccttac ccttctccag tctggaattt ctcttgctgg atccttcgtt    240

ccaggtggaa ctttcgtggc tccaatcatc aacatggtga ttggatggct ttggccacac    300

aagaacaaga acgctgatac cgagaacctc attaacctca tcgattccga gattcagaag    360

cagcttaaca aggctcttct cgatgctgat aggaacgagt ggtcctctta ccttgagtcc    420

atcttcgatt cctccaacaa cctcaacggt gctattgtgg atgctcagtg gagtggaact    480

gttaacacta ccaacaggac ccttagaaac ccaaccgagt ccgattacac caacgttgtg    540

accaacttca ttgctgctga tggcgatatt gccaacaacg agaaccacat catgaacgga    600

aacttcgatg ttgctgctgc tccatacttc gttattggag ctaccgctag attcgctgct    660

atgcaatcct acatcaagtt ctgcaacgct tggattgaca aagtgggact ttccgatgct    720

caacttacta cccagaaggc taaccttgat aggaccaagc agaacatgag gaacgctatc    780

cttaactaca cccagcaggt tatgaaggtg ttcaaggact ccaagaacat gccaaccatt    840

ggcaccaaca agttctctgt ggacacctac aacgtgtaca tcaagggcat gaccttgaac    900

gtgctcgata ttgtggctat ttggccatcc ctttacccag atgattacac ctctcagact    960

gctcttgagc aaactagggt gaccttctct aacatggtgg gtcaagaaga aggtactgac   1020

ggatctctca ggatctacaa caccttcgac tcattctctt accagcactc cccaatccca   1080

aacaacaacg tgaacctcat ctcctactac aacgacgagc ttcagaacct tgagcttgga   1140

gtttacaccc caccaaagaa gggatctgga tactcttacc catacggctt cgtgcttaac   1200

tacgccaact ccaagtacaa gtacggcgat tctaacgatc cagagtctct tggaggactt   1260

tctacccttt ccgctccaat tcaacaggtt aacgctgcta cccagaactc taagtacctc   1320

gatggcgaga ttcttaacgg aattggagct tcccttccag gatattgcac tactggatgc   1380

tctccaactg aaccaccatt ctcttgcact tctaccgcta acggatacaa ggcttcttgc   1440

aacccatctg acaccaacca gaagatcaac gctctttacc cattcactca ggctaacgtg   1500

aagggaaaca ccggaaagct tggagttctt gcttctctcg tgtcctacga tctcaaccca   1560

aagaacgtgt tcggagagct tgattccgat accaacaacg tgattctcaa gggaattcca   1620

gctgagaagg gctatttccc aaacaacgct aggccaaccg ttgtgaaaga gtggattaac   1680

ggcgcttctg ctgttccact tgattctggc aacacccttt tcatgaccgc tactaacctt   1740

actgctaccc agtacaggat taggatcaga tacgccaacc caaactccaa cacccaaatc   1800
```

ggagttagga ttacccagaa cggatccctt atttcttctt ccaacctcac cctttactct 1860
accaccgaca tgaacaacac ccttccactt aacgtgtacg tgattggaga gaacggaaac 1920
tacacccttc aggaccttta caacaccacc aacgtgcttt ctaccggtga tattaccctc 1980
caaatcaccg gtggagatca gaagattttc atcgacagga tcgagttcgt tccaactatg 2040
ccagttccag gcaacactaa caacaacaac ggaaacaaca atggcaacaa taacccacca 2100
catcatgtgt gtgctattgc tggaactcag cagtcttgtt ctggaccacc aaagttcgag 2160
caagtgtccg atcttgagaa gattaccacc caggtgtaca tgcttttcaa gtcctcccca 2220
tacgaagaac ttgctcttga ggtgtcctct taccagattt cccaagtggc tcttaaggtg 2280
atggctctct ccgatgaact tttctgcgaa gagaagaacg tgcttaggaa gcttgtgaac 2340
aaggccaagc aacttcttga ggcttccaac cttcttgttg gaggcaactt cgagactact 2400
cagaactggg tgttgggaac taacgcctac atcaactacg attccttcct cttcaacggt 2460
aactaccttt ctcttcagcc agcttctgga ttcttcacct cctacgccta ccaaaagatt 2520
gatgagtcca cccttaagcc atacaccagg tacaaggtgt caggattcat tggacagtct 2580
aaccaggtgg agcttatcat ttccagatac ggcaaagaga tcgacaagat cctcaacgtt 2640
ccatatgctg gaccacttcc aattaccgct gatgcttcca ttacttgctg cgctccagaa 2700
attggacaat gcgacggcga acagtctgat tctcacttct tcaactactc catcgatgtg 2760
ggtgctcttc atccagaact caacccagga attgagatcg gactcaagat cgttcagtcc 2820
aacggttaca tcaccatttc caacctcgag atcattgagg aaaggccact taccgagatg 2880
gaaatccagg ctgtgaatag gaagaaccag aagtgggaga gggaaaagct tcttgagtgc 2940
gcttctattt ctgagcttct ccagcctatc atcaaccaga ttgactccct cttcaaggat 3000
ggaaactggt acaacgatat ccttccacat gtgacctacc aggacctcaa gaacattatc 3060
atcccagagc ttccaaagct taagcactgg ttcattgaga acttgcctgg tgagtaccat 3120
gagatcgagc agaagatgaa ggaagctctc aagtacgctt tcacccagct tgatgagaag 3180
aacctcattc acaacggaca tttcaccacc aacctcattg attggcaagt tgagggtgat 3240
gctcagatga aggtgttgga gaacgatgct cttgctcttc agctcttcaa ctgggatgct 3300
tctgcttccc agtccattaa catcctcgag ttcgatgagg ataaggctta caagcttagg 3360
gtttacgctc aaggatctgg aactatccag ttcggaaact gcgaagatga ggccattcag 3420
ttcaacacca acagcttcat ctaccaagag aagatcgtgt acttcgatac ccccatctgtg 3480 aaccttcaca ttcagtctga gggatccgag ttcattgtgt cctccatcga tctcattgag 3540
ctttccgacg accagtga 3558

<210> SEQ ID NO 5
<211> LENGTH: 3561
<212> TYPE: DNA
<213> ORGANISM: Bacillus thuringiensis

<400> SEQUENCE: 5
atggattgta atttacaatc acaacaaaat attccttata atgtattagc aataccagta 60
tctaatgtta atgcgttggt tgatacagct ggagatttaa aaaaagcatg ggaagaattt 120
caaaaaactg gttctttttc attaacagct ttacaacaag gattttctgc ctcacaagga 180
ggagcattca attatttaac attattacaa tcaggaatat cattagctgg ttcttttgtc 240
cctggaggta cttttgtagc acccattgtt aatatggtta ttggttggtt atggccacat 300

-continued

```
aaaaacaaga cagcggatac agaaaattta ataaaattaa ttgatgaaga aattcaaaaa    360
caattaaaca aagccttatt agaccaagat agaaacaatt ggacctcttt tttagaaagt    420
atatttgata cttcagctac agtaagtaat gcaattatag atgcacagtg gtcaggtact    480
gtagatacta caaatagaca acaaaaaact ccaacaacat cagattatct aaatgttgtt    540
ggaaaatttg attcagcgga ttcttcaatt ataactaatg aaaatcaaat aatgaatggc    600
aactttgacg tagctgcagc accctatttt gttataggag caacattacg tctttcatta    660
tatcaatctt atattaaatt ttgtaatagt tggattgatg cagttggatt tagtacaaat    720
gatgctaata cacaaaaagc taatttagct cgtacgaaat taactatgcg tactacaatt    780
aatgaatata cacaaagagt tatgaaagtt tttaaagatt ccaagaatat gcctacaata    840
ggtactaata aatttagtgt tgatgcttat aatgtatatg ttaaaggaat gacattaaat    900
gttttagata tggtagcaat atggtcttca ttatatccaa atgattatac ttcacaaaca    960
gccatagaac aaacacgtgt cactttttca aatatggttg gacaagaaga aggtacagat   1020
ggaaccctaa aaatttacaa tacttttgat tctcttagtt atcaacatag cctaatacct   1080
aataataatg ttaatttaat ttcttattat actgatgaat tgcaaaatct agaattagca   1140
gtatatactc ctaaaggtgg aagtggatac gcttatcctt atggatttat tttaaattat   1200
gcaaacagca actacaaata tggtgataat gatccaacag gcaaaccatt aaataaacaa   1260
gatggaccta tacaacaaat aaatgcagca actcaaaaca gtaaatatct agatggagaa   1320
acaataaatg gaataggggc atccttacct ggttattgta ctacaggatg ttcagcaaca   1380
gaacaacctt ttagttgtac ttctactgct aatagctata aagcaagctg taatccttca   1440
gatactaatc aaaaaattaa tgctttatat gcttttacac aaactaatgt aaagggaagc   1500
acggggaaat taggagtact ggcaagtctt gttccatatg atttaaatcc taaaaatgta   1560
tttggtgaat tagattcaga tacaaataat gttatcttaa aaggaattcc tgcagaaaaa   1620
gggtattttc ctaataatgc gcgacctact gttgtaaaag aatggattaa tggtgcaagt   1680
gctgtaccat tttattcagg aaatacttta tttatgacgg ctacgaattt aacagctact   1740
caatataaaa ttagaatacg ttatgcaaat ccaaattcag atactcaaat cggtgtacta   1800
attacgcaaa atggttctca aatttccaat agtaatctaa cactttatag tactactgat   1860
tcaagtatga gtagtaattt accacaaaat gtatatgtca caggggaaaa tggaaattat   1920
acacttctag atttatatag tactactaat gttttatcaa caggagatat tacattaaaa   1980
cttacaggag gaaatcaaaa aatatttatt gatcgaatag aatttattcc tactatgcct   2040
gtacctgctc ctactaataa cactaataac aataacggcg ataacggcaa taacaatccc   2100
ccacaccacg gttgtgcaat agctggtaca caacaacttt gttctggacc acctaagttt   2160
gaacaagtaa gtgatttaga aaaaattaca acgcaagtat atatgttatt caaatcttct   2220
tcgtatgaag aattagctct aaaagtttct agctatcaaa ttaatcaagt ggcattgaaa   2280
gttatggcac tatctgatga aaagttttgt gaagaaaaaa gattgttacg aaaattagtc   2340
aataaagcaa accaattact agaagcacgt aacttactag taggtggaaa ttttgaaaca   2400
actcaaaatt gggtacttgg aacaaatgct tatataaatt atgattcgtt tttatttaat   2460
ggaaattatt tatccttaca accagcaagt ggatttttca catcttatgc ttatcaaaaa   2520
atagatgagt caacattaaa accatataca cgatataaag tttctggatt cattgggcaa   2580
agtaatcaag tagaacttat tatttctcgt tatggaaaag aaattgataa aatattaaat   2640
gttccatatg cagggcctct tcctattact gctgatgcat cgataacttg ttgtgcacca   2700
```

```
gaaatagacc aatgtgatgg ggggcaatct gattctcatt tcttcaacta tagcatcgat   2760

gtaggtgcac ttcacccaga attaaaccct ggcattgaaa ttggtcttaa aattgtgcaa   2820

tcaaatggtt atataacaat tagtaatcta gaaattattg aagaacgtcc acttacagaa   2880

atggaaattc aagcagtcaa tcgaaaagat caaaaatgga aaagagaaaa acttctagaa   2940

tgtgcaagtg ttagtgaact tttacaacca atcattaatc aaatcgattc attgttcaaa   3000

gatgcaaact ggtataatga tattcttcct catgtcacat atcaaactct aaaaaatatt   3060

atagtacccg atttaccaaa attaaaacat tggttcatag atcatctccc aggtgaatat   3120

catgaaattg aacaaaaaat gaaagaagct ctaaaacatg catttacaca attagacgag   3180

aaaaatttaa tccacaatgg tcactttgca actaacttaa tagattggca agtagaaggt   3240

gatgctcgaa tgaaagtatt agaaaataat gctttggcat tacaactttc caattgggat   3300

tctagtgttt cacaatctat tgatatatta gaatttgatg aagataaagc atataaactt   3360

cgcgtatatg ctcaaggaag cggaacaatc caatttggaa actgtgaaga tgaagccatc   3420

caatttaata caaactcatt cgtatataaa gaaaaaataa tctatttcga taccccatca   3480

attaacttac acatacaatc agaaggttct gaattcgttg taagtagtat cgacctcgtt   3540

gaattatcag acgacgaata a                                             3561
```

<210> SEQ ID NO 6
<211> LENGTH: 3558
<212> TYPE: DNA
<213> ORGANISM: Bacillus thuringiensis

<400> SEQUENCE: 6

```
atggattgta atttacaatc acaacaaaat attccatata atgtattagc aataccagta     60

tctaatgtta attcgttgac tgatacagtt ggagatttaa aaaaagcatg ggaagaattt    120

caaaaaactg gttctttttc attaacagct ttacaacaag gattttctgc ttcacaagga    180

ggaacattca attatttaac attactacaa tcaggaatat cattagctgg ttcttttgtt    240

cctggaggta cttttgtagc acctattatt aatatggtta ttggttggtt atggccacat    300

aaaaacaaaa atgcggatac agaaaattta ataaatttaa ttgattcaga aattcaaaaa    360

caattaaaca aagctttatt agatgcagat agaaatgagt ggagctctta tttagaatct    420

atatttgatt cttcaaataa cctaaatggt gcaattgtag atgcacagtg gtcaggcact    480

gtaaatacta caaatagaac actaagaaat ccaacagaat cagattatac aaatgttgtt    540

acaaatttta ttgcagcgga tggtgacatt gcaaataatg aaaatcacat aatgaatggc    600

aactttgacg tagctgcagc accttatttt gttataggag caacagcacg ttttgcagca    660

atgcaatctt atattaaatt ttgtaatgct tggattgata aagttggatt gagtgacgca    720

cagcttacta cacaaaaggc taatttagat cgcacgaaac aaaatatgcg taatgcaatt    780

cttaactata cacaacaagt tatgaaagtt tttaaagatt ccaaaaatat gcctacaata    840

ggtactaata aatttagtgt tgatacctat aatgtatata ttaaaggaat gacattaaat    900

gttttagata ttgtagcaat atggccttca ttatatccag atgattatac ttcacaaaca    960

gccttagaac aaacacgtgt cactttttca aatatggttg gccaagaaga aggtacagat   1020

ggaagcctaa gaatttacaa tacttttgat tcttttagtt atcaacatag tccaatacct   1080

aataataatg ttaatttaat ttcttattat aatgatgaat tacaaaatct agaattagga   1140

gtatataccc ctcctaaaaa aggaagtgga tactcttatc cttatggatt tgttttaaat   1200
```

```
tatgcaaaca gtaaatataa atatggtgat agcaatgatc cagaatctct aggaggatta   1260

tctacactat ctgcacctat acaacaagtt aatgcagcaa ctcaaaacag taaatatcta   1320

gatggagaaa tcctaaatgg aataggagca tccttacctg gttattgtac tacaggatgt   1380

tcaccaacag aaccaccttt tagttgtact tctaccgcta atggctataa agcaagctgt   1440

aatccttcag atacaaatca aaaaattaac gctttatatc cttttacaca agctaatgta   1500

aagggaaaca caggaaaatt aggagtactg gcaagtcttg tttcatatga tttaaatcct   1560

aaaaatgtat ttggtgaatt agattcagat acaaataatg ttatcttaaa aggaattcct   1620

gcagaaaaag gatattttcc taataatgcg cgtcctactg ttgtaaaaga atggattaat   1680

ggtgcaagtg ctgtaccact tgattcagga aataccttat ttatgacggc tacgaattta   1740

acagctactc aatatagaat tagaatacgt tatgcaaatc caaattcaaa tactcaaatc   1800

ggtgtacgaa ttacacaaaa tggttctcta atttccagta gtaatctaac actttatagt   1860

actactgata tgaataatac tttaccacta aatgtatatg taataggaga aaatggaaat   1920

tatacacttc aagatttata taatactact aatgttttat caacaggaga tattacatta   1980

caaattacag gaggagatca aaaaatattt attgatcgaa tagaatttgt tcctactatg   2040

cctgtacctg gtaatactaa caacaataac ggtaataata acggtaataa taatcccccca   2100

caccacgttt gtgcaatagc tggtacacaa caatcttgtt ctggaccgcc caaatttgaa   2160

caagtaagtg atttagaaaa aattacaaca caagtatata tgttattcaa atcttctccg   2220

tatgaagaat tagctctaga agtttccagc tatcaaatta gtcaagtagc attaaaagtt   2280

atggcattat ctgatgaact attttgtgaa gaaaaaaacg tattacgaaa attagtcaat   2340

aaagcaaaac aattattaga agcaagtaac ttactagtag gtggaaattt tgaaacaact   2400

caaaattggg tacttggaac aaatgcttat ataaattatg attcgttttt atttaatgga   2460

aattatttat ctttacaacc agcaagtgga tttttcacat cttatgctta tcaaaaaata   2520

gatgagtcaa cattaaaacc atatacacga tataaagttt ctgggttcat tgggcaaagt   2580

aatcaagtag aacttattat ttctcgttat ggaaaagaaa ttgataaaat attaaatgtt   2640

ccatatgcag gacctcttcc tatcactgct gatgcatcaa taacttgttg tgcaccagaa   2700

ataggccaat gtgatgggga acaatctgat tctcatttct ttaactatag catcgatgta   2760

ggtgcacttc acccagaatt aaaccctggc attgaaattg gtcttaaaat tgtgcaatca   2820

aatggttata taacaattag taatctagaa attattgaag aacgtccact tacagaaatg   2880

gaaattcaag cagtcaatcg aaaaaatcaa aaatgggaaa gagaaaaact tctagaatgt   2940

gcaagtatta gtgaactttt acaaccaatt attaatcaaa tcgattcatt gtttaaagat   3000

ggaaactggt ataatgatat tcttcctcat gtcacatatc aagatttaaa aaatattata   3060

atacccgagt taccaaaatt aaaacattgg ttcatagaga atctcccagg tgaatatcat   3120

gaaattgaac aaaaaatgaa agaagctcta aaatatgcat ttacacaatt agacgagaaa   3180

aatttaatcc acaatggtca ctttacaact aacttaatag attggcaagt agaaggtgat   3240

gctcaaatga aagtattaga aaatgatgct cttgcattac aacttttcaa ctgggatgct   3300

agtgcttcac aatctataaa tatattagaa tttgatgaag ataaggcata taaacttcgc   3360

gtatatgctc aaggaagcgg aacaatccaa tttggaaact gtgaagatga agctatccaa   3420

tttaatacaa actcattcat atatcaagaa aaaatagtct atttcgatac cccatcagtt   3480

aatttacaca tacaatcaga aggttctgaa tttattgtaa gtagtatcga tctaattgaa   3540

ttatcagacg accaataa                                                 3558
```

```
<210> SEQ ID NO 7
<211> LENGTH: 4
<212> TYPE: PRT
<213> ORGANISM: Artificial sequence
<220> FEATURE:
<223> OTHER INFORMATION: ER targeting peptide

<400> SEQUENCE: 7

Lys Asp Glu Leu
1
```

USE OF CRY14 FOR THE CONTROL OF NEMATODE PESTS

CROSS REFERENCE TO RELATED APPLICATION

This application is a continuation of U.S. patent application Ser. No. 16/468,569 filed Jun. 11, 2019, which is a National Stage Entry of PCT/US2017/068070 and claims the benefit of U.S. Provisional Application No. 62/438,420, filed Dec. 22, 2016, the contents of all which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "181400US03_SEQLIST.txt," created on Mar. 22, 2021, and having a size of 40 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are methods for the control of nematode pests using Cry14.

BACKGROUND OF THE INVENTION

Nematodes are active, flexible, elongate, organisms that live on moist surfaces or in liquid environments, including films of water within soil and moist tissues within other organisms. Many species of nematodes have evolved to be very successful parasites of plants and animals and are responsible for significant economic losses in agriculture and livestock and for morbidity and mortality in humans (Whitehead (1998) Plant Nematode Control. CAB International, New York).

It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) Plant and Soil Nematodes: Societal Impact and Focus for the Future. The Committee on National Needs and Priorities in Nematology. Cooperative State Research Service, US Department of Agriculture and Society of Nematologists). In the high-acreage crop markets, nematode damage is greatest in soybeans and cotton. There are however, dozens of additional crops that suffer from significant nematode infestation including potato, pepper, onion, citrus, coffee, sugarcane, greenhouse ornamentals and golf course turf grasses.

Nematodes are known to affect the yield, growth, and health of crops and plants. The physiological changes in the host plant's roots caused by larvae and/or adult nematodes can lead to the formation of galls, which causes a disruption of the vascular system of the plant's roots. Root elongation can stop completely and inadequate supply of water and nutrients provided by the reduced root system can result, causing foliage chlorosis and/or wilt, as well as stunting of growth, any of which can result in low yield or death. In addition, nematodes can cause physiological effects leading to an increase in the susceptibility of plant roots to bacteria and/or fungi attack, including bacteria and/or fungi the plant would otherwise resist. Such attack can lead to extensive secondary decay and rotting.

The root lesion nematode *Pratylenchus brachyurus* has become an increasingly important pathogen of soybean. It has a broad host range and is widely distributed in tropical and subtropical regions, especially in Brazil, Africa, and the Southern United States. *Pratylenchus brachyurus* has become a concern among cotton and soybean growers in the Brazilian Cerrado region and is considered the main nematode pathogen of soybean in the region. In soybean, this nematode can reduce yields 30 to 50%, with greater damage being observed on sandy soils. There are currently no *P. brachyurus*-resistant soybean varieties identified to date. Although several soybean genotypes have been studied for *Pratylenchus brachyurus* resistance, and some cultivars identified with increased tolerance, breeding resistant cultivars against *P.brachyurus* is difficult due to the fact that this nematode is polyphagous and lacks a close interaction with its hosts (Machado (2014) Current Agricultural Science and Technology 20:26-35; Antonio et al. (2012) Soil productivity losses in area infested by the nematoid of the root lesions in Vera, MT. In: Brazilian Congress of Soy, 6, 2012, Cuiabá. Abstracts. Londrina: Embrapa Soja, 4pp; Rios et al. (2016) Ciência Rural 46:580-584; Lima et al., 2017, Chapter 6 in the book: Soybean—The Basis of Yield, Biomass and Productivity; Edited by Minobu Kasai, ISBN 978-953-51-3118-2, Print ISBN 978-953-51-3117-5, InTech; Inomoto et al. (2011) Sucessão de culturas sob pivô central para controle de fitonematoides: vação populacional, patogenicidade e estimativa de perdas. Tropical Plant Pathology 36:178-185).

Methods for controlling infestations by nematodes have been provided in several forms. Biological and cultural control methods, including plant quarantines, have been attempted in numerous instances. Genetic resistance to certain nematodes is available in some commercial cultivars (e.g., soybeans), but these are restricted in number and the availability of cultivars with both desirable agronomic features and resistance is limited. Furthermore, the production of nematode resistant commercial varieties by conventional plant breeding based on genetic recombination through sexual crosses is a slow process and is often further hampered by a lack of appropriate germplasm.

Chemical means of controlling plant parasitic nematodes continue to be essential for many crops which lack adequate natural resistance. However, chemical agents are often not selective, and some exert their effects on non-target organisms, effectively disrupting populations of beneficial microorganisms, for a period of time following application of the agent. Chemical agents may persist in the environment and only be slowly metabolized.

Thus, there exists a need for additional means for controlling nematode populations in agriculturally-important plants.

SUMMARY OF INVENTION

Compositions and methods for conferring nematicidal activity to plants, plant cells, tissues and seeds are provided. In particular, methods for killing or controlling a nematode pest population, particularly a lesion nematode such as *Pratylenchus* sp, e.g., *Pratylenchus brachyurus*, population, are provided. The invention further provides control of root knot nematode (*Meloidogyne* spp. soybean pest nematodes, including but not limited to *Meloidogyne incognita, Meloidogyne arenaria, Meloidogyne hapla*, or *Meloidogyne*

*javanica*, or any combination thereof), reniform nematode (*Rotylenchulus reniformis*) and Lance nematode (*Hoplolaimus* spp. such as *H. columbus, H. galeatus*, and *H. magnistylus*). The methods comprise contacting the nematode pest with a pesticidally-effective amount of a polypeptide comprising a nematicidal toxin, particularly a nematicidal toxin active against a *Pratylenchus* spp. nematode, e.g. *Pratylenchus brachyurus*, a root knot nematode, a reniform nematode, or a Lance nematode. In various embodiments, the nematicidal toxin comprises the amino acid sequence of SEQ ID NO:1 or 2, or pesticidally-effective variants or fragments thereof. In some embodiments, the method for protecting a plant or cell thereof from a nematode pest population, particularly a *Pratylenchus* spp. nematode, e.g. *Pratylenchus brachyurus*, a root knot nematode, a reniform nematode, or a Lance nematode, comprises expressing in a plant or cell thereof a nucleic acid encoding SEQ ID NO:1 or 2, or a variant or fragment thereof, wherein the nucleic acid is operably linked to a promoter capable of directing expression of the nucleic acid in a plant cell.

Further comprised are methods for increasing yield in a plant comprising growing in a field a plant or a seed thereof having stably incorporated into its genome a DNA construct comprising a nucleic acid operably linked to a promoter capable of directing expression of the nucleic acid in a plant cell, wherein the nucleic acid encodes SEQ ID NO:1 or 2, or a pesticidally-effective variant or fragment thereof.

The compositions and methods of the invention are useful for the production of organisms with enhanced nematode, e.g. *Pratylenchus* spp., root knot nematode, reniform nematode, or Lance nematode resistance or tolerance. These organisms and compositions comprising the organisms are desirable for agricultural purposes.

Elite soybean plants with EE-GM4 control *Pratylenchus brachyurus* in US greenhouse assays. Soybean plants expressing SEQ ID NO:2 ("EE-GM4") were compared to other elite soybean lines: one SCN susceptible Maturity Group (MG) 3 line ("THORNE"), one MG3 SCN susceptible line, one MG 6.2 SCN susceptible line and one MG9 SCN susceptible line ("Susc WT" shows the average for these 3 lines), one MG3 SCN resistant line (with the rhg1 resistance allele from PI88788, "SCN Res (PI88788)"), and one MG 6.2 SCN resistant line with the rhg1 and Rhg4 SCN resistance from Peking ("SCN Res (Peking)"). Plotted are the average numbers of *Pratylenchus* in roots 30 days after infestation (5 plants per entry), also showing the variation observed across variaties (as typically seen in greenhouse assays). Results show ~85% control of *Pratylenchus* across EE-GM4 lines. Soybean lines with native SCN resistance (from Peking or PI88788) do not control *Pratylenchus brachyurus*.

Figure 2:
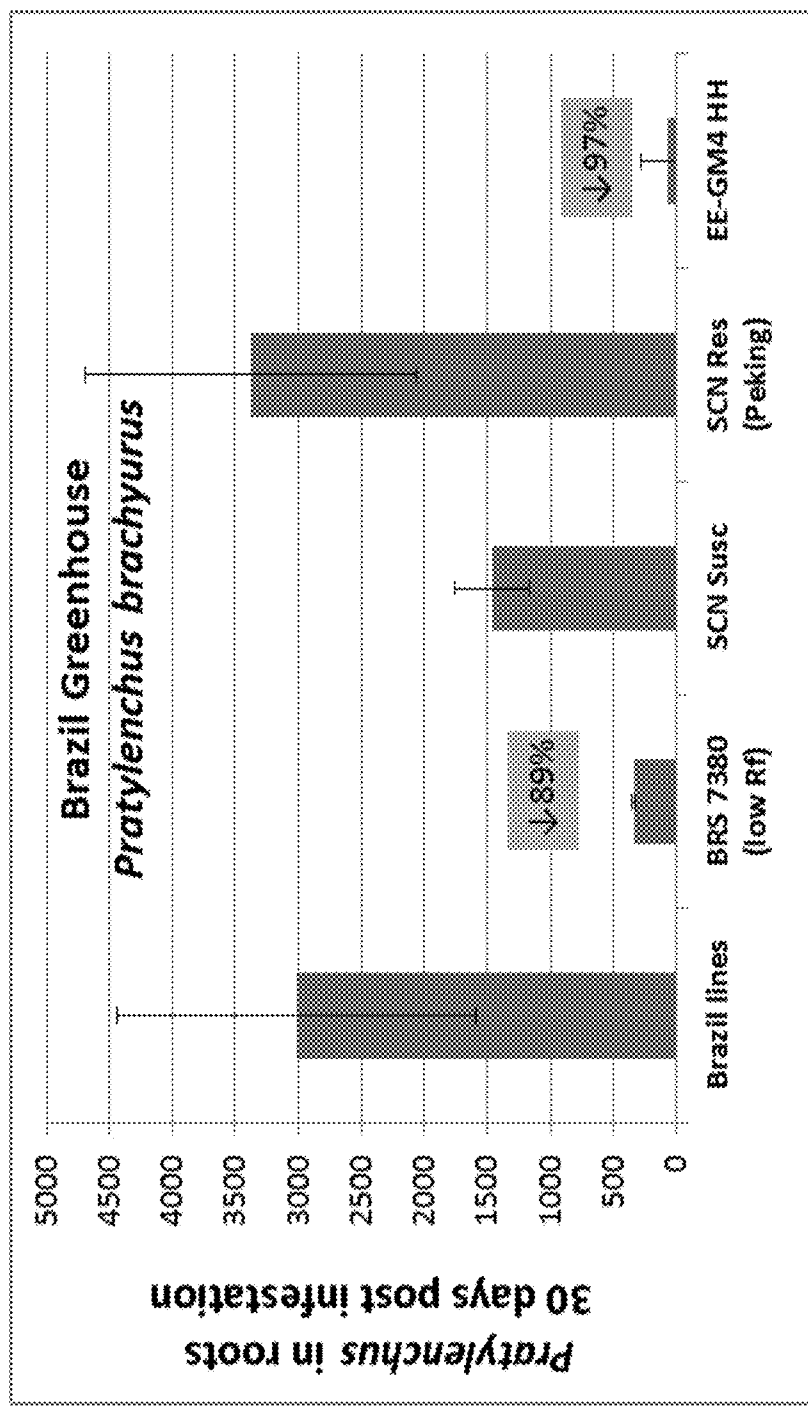

FIG. 2. *Pratylenchus* resistance greenhouse assay in Brazil

Soybean plants with EE-GM4 ("EE-GM4") significantly reduce *Pratylenchus brachyurus* in soybean roots. *Pratylenchus brachyurus* were isolated from local fields in Brazil. EE-GM4 plants (in two different US elite lines (both maturity group 6.2, one SCN-susceptible and one with Peking SCN-resistance ("EE-GM4")) and five Brazilian soybean lines, with limited *Pratylenchus* control ("Brazil lines"), one Brazilian line, labeled as low Rf (reproductive factor) for *Pratylenchus* ("BRS 7380 (low Rf)"), one US elite line (maturity group 6.2) that is SCN-susceptible ("SCN Susc") and one US elite line of MG 6.2 with Peking SCN-resistance ("SCN Res (Peking)") were evaluated for *Pratylenchus* control in a greenhouse assay in Brazil. Plotted are the averages of those entries, also showing the variation observed across varieties (as typically seen in greenhouse assays). One Brazilian soybean line (BRS 7380), showed ~89% reduction of *Pratylenchus*. EE-GM4 lines gave ~79% control of *Pratylenchus*. Soybean lines that carry Peking native resistance to SCN do not control *Pratylenchus brachyurus*.

DETAILED DESCRIPTION

The present invention is drawn to methods for regulating nematode resistance in organisms, particularly plants or plant cells. By "resistance" is intended that the nematode is killed upon ingestion or other contact with the polypeptides of the invention is impaired in the movement, feeding, reproduction, or other functions of the nematode. Controlling plant-parasitic nematode populations in a plant or seed thereof will improve nodulation, germination, root development, emergence, and health, including resistance to or protection from disease, including bacterial or fungal disease, which is an important benefit of methods disclosed and described herein. Thus, methods as described herein are useful for controlling nematode populations, particularly *Pratylenchus* spp. nematode populations, e.g., *Pratylenchus brachyurus*, root knot nematode, reniform nematode, or Lance nematode, which provide improved general plant health, nutrition and/or improved agronomical benefit of a plant and/or seed. Any benefit related to nematode population control, such as, for example, reduction in total number/area of nematodes, reduction in nematode eggs/area, or reduction in damage to the plant, can be an agronomical benefit of the present invention. Secondary benefits of controlling the nematode populations include, without limitation, improved root development (e.g., improved root or root hair growth), improved yield, faster emergence, improved plant stress management including increased stress tolerance and/or improved recovery from stress, increased mechanical strength, improved drought resistance, reduced fungal disease infection, and improved plant health. Combinations of any of these benefits can also be obtained.

The methods of the present invention involve transformation of organisms or use of organisms comprising a heterologous nucleotide sequence encoding a nematicidal protein of the invention. The methods described herein are useful for controlling or killing nematode pest populations and for producing compositions with nematicidal activity against nematode pests.

By "pesticidal toxin" or "pesticidal protein," or "nematicidal activity" or "nematicidal toxin" is intended a toxin that has activity against one or more nematode pests, including, but not limited to, *Pratylenchus* spp., including *Pratylenchus alleni, Pratylenchus brachyurus, Pratylenchus coffeae, Pratylenchus crenatus, Pratylenchus dulscus, Pratylenchus fallax, Pratylenchus flakkensis, Pratylenchus goodeyi, Pratylenchus hexincisus, Pratylenchus loosi, Pratylenchus minutus, Pratylenchus mulchandi, Pratylenchus musicola, Pratylenchus neglectus, Pratylenchus penetrans, Pratylenchus pratensis, Pratylenchus renformia, Pratylenchus scribneri, Pratylenchus thornei, Pratylenchus vulnus*, and *Pratylenchus zeae*. Nematicidal proteins include amino acid sequences deduced from the full-length nucleotide sequences disclosed herein, and amino acid sequences that are shorter than the full-length sequences, either due to the use of an alternate downstream start site, or due to processing that produces a shorter protein having nematicidal activity. Processing may occur in the organism the protein is expressed in, or in the pest after ingestion of the protein.

In specific embodiments, the nematicidal protein comprises a Cry14 protein. In various embodiments, the Cry14 protein is Cry14Aa1 (GENBANK accession number AAA21516) or Cry14Ab1 (GENBANK accession number KC156652). In some embodiments, the Cry14Aa1 protein encompasses the amino acid sequence set forth in SEQ ID NO:1, as well as variants and fragments thereof. In other embodiments, the Cry14Ab1 protein encompasses the amino acid sequence set forth in SEQ ID NO:2, as well as variants and fragments thereof. Exemplary nucleotide sequences encoding SEQ ID NO:1 are set forth in SEQ ID NO:3 and 5. Exemplary nucleotide sequences encoding SEQ ID NO:2 are set forth in SEQ ID NO:4 and 6.

Thus, provided herein are methods for killing or controlling a nematode pest population, e.g. a *Pratylenchus* spp. population, e.g., *Pratylenchus brachyurus*, root knot nematode, reniform nematode, or Lance nematode, comprising contacting the nematode pest, or exposing the nematode pest to, a composition comprising the nematicidal toxin of the invention. In specific embodiments, the nematicidal protein comprises the Cry14 protein set forth in SEQ ID NO:1 or 2, as well as variants and fragments thereof.

Isolated Nucleic Acid Molecules, and Variants and Fragments Thereof

One aspect of the invention pertains to isolated, recombinant or chimeric nucleic acid molecules comprising nucleotide sequences encoding nematicidal proteins and polypeptides or biologically active portions thereof, as well as nucleic acid molecules sufficient for use as hybridization probes to identify nucleic acid molecules encoding proteins with regions of sequence homology. Also encompassed herein are nucleotide sequences capable of hybridizing to the nucleotide sequences of the invention under stringent conditions as defined elsewhere herein. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The term "recombinant" encompasses polynucleotides or polypeptides that have been manipulated with respect to the native polynucleotide or polypeptide, such that the polynucleotide or polypeptide differs (e.g., in chemical composition or structure) from what is occurring in nature. An "isolated nucleic acid (sequence/molecule)" or "isolated DNA (sequence/molecule)", as used herein, refers to a nucleic acid or DNA (sequence/molecule) which is no longer in the natural environment it was isolated from, e.g., the nucleic acid sequence in another bacterial host or in a plant genome, or a nucleic acid or DNA (sequence/molecule) fused to DNA or nucleic acid (sequence/molecule) from another origin, such as when contained in a chimeric gene under the control of a (heterologous) plant-expressible promoter. Any nucleic acid or DNA of this invention, including any primer, can also be non-naturally-occurring, such as a nucleic acid or DNA with a sequence identical to a sequence occurring in nature, but having a label (missing from the naturally-occurring counterpart), or with a sequence having at least one nucleotide addition or replacement or at least one internal nucleotide deletion compared to a naturally-existing nucleotide, or with a sequence having a sequence identity below 100% (not identical) to a naturally-existing nucleic acid or DNA or a fragment thereof, or a nucleic acid or DNA with a sequence consisting of nucleotide sequences from different origins that do not occur together in nature (a chimeric or hybrid DNA), or a man-made synthetic nucleic acid or DNA with a sequence different from the natural nucleic acid or DNA or a fragment thereof.

An isolated, recombinant or chimeric nucleic acid (or DNA) is used herein to refer to a nucleic acid (or DNA) that is no longer in its natural environment, for example in an in vitro or in a recombinant bacterial or plant host cell. In some embodiments, an isolated, recombinant or chimeric nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various embodiments, a delta-endotoxin protein that is substantially free of cellular material includes preparations of protein having less than about 30%, 20%, 10%, or 5% (by dry weight) of non-delta-endotoxin protein (also referred to herein as a "contaminating protein"). In some embodiments, the recombinant nucleic acid of the invention comprises one or more nucleotide substitutions relative to SEQ ID NO:3-6, or a variant or fragment thereof.

Nucleotide sequences encoding the proteins of the present invention include the sequence set forth in SEQ ID NO:3-6, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the nematicidal proteins encoded by these nucleotide sequences are set forth in SEQ ID NO:1 and 2.

Nucleic acid molecules that are fragments of these nucleotide sequences encoding nematicidal proteins are also encompassed by the present invention. By "fragment" is intended a portion of the nucleotide sequence encoding a nematicidal protein. A fragment of a nucleotide sequence may encode a biologically active portion of a nematicidal protein, or it may be a fragment that can be used as a hybridization probe or PCR primer using methods disclosed below. Nucleic acid molecules that are fragments of a nucleotide sequence encoding a nematicidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a nematicidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the nematicidal protein and, hence, retain pesticidal activity against a nematode pest. Thus, biologically-active fragments of the polypeptides disclosed herein are also encompassed. By "retains activity" is intended that the fragment will have at least about 30%, at least about 50%, at least about 70%, 80%, 90%, 95% or higher of the pesticidal activity of the nematicidal protein. Methods for measuring nematicidal activity are well known in the art and are also described herein.

A fragment of a nucleotide sequence encoding a nematicidal protein that encodes a biologically active portion of a protein of the invention will encode at least about 15, 25, 30, 50, 75, 100, 125, 150, 175, 200, 250, 300, 350, 400, 450, 500, 550, 600, 650, 700, 750, 800, 850, 900, 950, 1000, 1050, 1100, or 1150 contiguous amino acids, or up to the total number of amino acids present in a full-length nematicidal protein of the invention. In some embodiments, the fragment is a proteolytic cleavage fragment. For example, the proteolytic cleavage fragment may have an N-terminal or a C-terminal truncation of at least about 30 amino acids, at least about 40 amino acids, at least about 50, at least about 100 amino acids, about 120, about 130, about 140, about 150, or about 160 amino acids relative to SEQ ID NO:1 or 2. In some embodiments, the fragments encompassed herein result from the removal of the C-terminal crystallization domain, e.g., by proteolysis, or by insertion of a stop codon in the coding sequence. In further embodiments, the fragments encompassed herein comprise an N-terminal truncation and the N-terminal truncations may comprise a methionine residue at the truncated N-terminus.

In various embodiments, the nucleic acid of the invention comprises a degenerate nucleic acid of SEQ ID NO:3-6, wherein said degenerate nucleotide sequence encodes the same amino acid sequence as SEQ ID NO:1 or 2.

Preferred nematicidal proteins of the present invention are encoded by a nucleotide sequence sufficiently identical to the nucleotide sequence of SEQ ID NO:3-6, or the nematicidal proteins are sufficiently identical to the amino acid sequence set forth in SEQ ID NO:1 or 2. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., the sequence disclosed herein as any of SEQ ID NO:1-6). The percent identity between two sequences can be determined using techniques similar to those described below, with or without allowing gaps. In calculating percent identity, typically exact matches are counted. A gap, i.e. a position in an alignment where a residue is present in one sequence but not in the other, is regarded as a position with non-identical residues.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to nematicidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, CA). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) CABIOS 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, CA, USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the nematicidal protein encoding nucleotide sequences include those sequences that encode the nematicidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the nematicidal proteins disclosed in the present invention as discussed below. Variant proteins encompassed by the present invention are biologically active, that is they continue to possess the desired biological activity of the native protein, that is, pesticidal activity against a nematode pest. By "retains activity" is intended that the variant will have at least about 30%, at least about 50%, at least about 70%, or at least about 80% of the pesticidal activity of the native protein. Methods for measuring pesticidal activity against a nematode pest are well known in the art and described elsewhere herein.

The skilled artisan will further appreciate that changes can be introduced by mutation of the nucleotide sequences of the invention thereby leading to changes in the amino acid sequence of the encoded nematicidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a nematicidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity against a nematode pest to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention (e.g., at least about 70%, at least about 75%, 80%, 85%, 90%, 95% or more sequence identity across the entirety of the reference sequence) and having or conferring pesticidal activity against a nematode pest. See, for example, Sambrook and Russell (2001) *Molecular Cloning: A Laboratory Manual*. (Cold Spring Harbor Laboratory Press, Cold Spring Harbor, NY) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known nematicidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a nematicidal protein of the invention or a fragment or variant thereof. Methods for the preparation of probes for hybridization are generally known in the art and are disclosed in Sambrook and Russell, 2001, supra herein incorporated by reference.

For example, an entire nematicidal sequence disclosed herein, or one or more portions thereof, may be used as a probe capable of specifically hybridizing to corresponding nematicidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism or sample by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, New York).

Thus, the present invention encompasses probes for hybridization, as well as nucleotide sequences capable of hybridization to all or a portion of a nucleotide sequence of the invention (e.g., at least about 300 nucleotides, at least about 400, at least about 400, 450, 500, 1000, 1200, 1500, 2000, 2500, 3000, 3500, or up to the full length of a nucleotide sequence disclosed herein). Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1× SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, New York).

Isolated Proteins and Variants and Fragments Thereof

Nematicidal proteins are also encompassed within the present invention. By "nematicidal protein" is intended a protein having the amino acid sequence set forth in SEQ ID NO:1 or 2. Fragments, biologically active portions, and variants thereof are also provided, and may be used to practice the methods of the present invention. An "isolated protein" or a "recombinant protein" is used to refer to a protein that is no longer in its natural environment, for example in vitro or in a recombinant bacterial or plant host cell. In some embodiments, the recombinant protein is a variant of SEQ ID NO:1 or 2, wherein the variant comprises at least one amino acid substitution, deletion, or insertion relative to SEQ ID NO:1 or 2.

"Fragments" or "biologically active portions" include polypeptide fragments comprising amino acid sequences sufficiently identical to the amino acid sequence set forth in SEQ ID NO:1 or 2, and that exhibit pesticidal activity against a nematode pest. A biologically active portion of a nematicidal protein can be a polypeptide that is, for example, 10, 25, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, or more amino acids in length. Such biologically active portions can be prepared by recombinant techniques and evaluated for pesticidal activity against a nematode pest. Methods for measuring pesticidal activity against a nematode pest are well known in the art (see, for example, U.S. Patent Application Publication No. US 20160066584) and described elsewhere herein. As used here, a fragment comprises at least 8 contiguous amino acids of SEQ ID NO:1 or 2. The invention encompasses other fragments, however, such as any fragment in the protein greater than about 10, 20, 30, 50, 100, 150, 200, 250, 300, 350, 400, 450, 500, 550, 600, 650, 700, 750, 800, 850, 900, 950, 1000, 1050, 1100, 1150, 1200, 1250, 1300, 1350 or more amino acids in length.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:1 or 2. Variants also include polypeptides encoded by a nucleic acid molecule that hybridizes to the nucleic acid molecule of SEQ ID NO:3-6, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity against a nematode pest. In some embodiments, the variants have improved activity relative to the native protein. Methods for measuring pesticidal activity against a nematode pest are well known in the art (see, for example, US Patent Application Publication No. US 20160066584) and described elsewhere herein.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined apriori which of these codons are used naturally in the bacterium. Thus, it is understood that use of one of the alternate methionine codons may also lead to generation of nematicidal proteins. These nematicidal proteins are encompassed in the present invention and may be used in the methods of the present invention. It will be understood that, when expressed in plants, it will be necessary to alter the alternate start codon to ATG for proper translation.

In various embodiments of the present invention, nematicidal proteins include amino acid sequences deduced from the full-length nucleotide sequences disclosed herein, and amino acid sequences that are shorter than the full-length sequences due to the use of an alternate downstream start site.

Antibodies to the polypeptides of the present invention, or to variants or fragments thereof, are also encompassed. Methods for producing antibodies are well known in the art (see, for example, Harlow and Lane (1988) Antibodies: A Laboratory Manual, Cold Spring Harbor Laboratory, Cold Spring Harbor, NY; U.S. Pat. No. 4,196,265).

Thus, one aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NO:1 or 2 or a fragment thereof. In another embodiment, the antibody specifically binds to a fusion protein comprising an amino acid sequence selected from the amino acid sequence set forth in SEQ ID NO:1 or 2 or a fragment thereof. In various embodiments, the antibody that specifically binds to the protein of the invention or a fusion protein comprising the protein of the invention is a non-naturally occurring antibody.

Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

The antibodies of the invention may be contained within a kit useful for detection of the protein or peptide molecules of the invention. The invention further comprises a method of detecting the protein or peptide molecule of the invention (particularly a protein encoded by the amino acid sequence set forth in SEQ ID NO:1 or 2, including variants or fragments thereof that are capable of specifically binding to the antibody of the invention) comprising contacting a sample with the antibody of the invention and determining whether the sample contains the protein or peptide molecule of the invention. Methods for utilizing antibodies for the detection of a protein or peptide of interest are known in the art.

Altered or Improved Variants

It is recognized that DNA sequences of a nematicidal protein may be altered by various methods, and that these alterations may result in DNA sequences encoding proteins with amino acid sequences different than that encoded by a nematicidal protein of the present invention. This protein may be altered in various ways including amino acid substitutions, deletions, truncations, and insertions of one or more amino acids of SEQ ID NO:1 or 2, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a nematicidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity against a nematode pest. However, it is understood that the ability of a nematicidal protein to confer pesticidal activity against a nematode pest may be improved by the use of such techniques upon the compositions of this invention. For example, one may express a nematicidal protein in host cells that exhibit high rates of base misincorporation during DNA replication, such as XL-1 Red (Stratagene, La Jolla, CA). After propagation in such strains, one can isolate the DNA (for example by preparing plasmid DNA, or by amplifying by PCR and cloning the resulting PCR fragment into a vector), culture the nematicidal protein mutations in a non-mutagenic strain, and identify mutated genes with pesticidal activity against a nematode pest, for example by performing an assay to test for pesticidal activity against a nematode pest. Such assays can include contacting plants with one or more pests and determining the plant's ability to survive and/or cause the death of the pests. See, for example, US Patent Application Publication No. US 20160066584).

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different nematicidal protein coding regions can be used to create a new nematicidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered nematicidal proteins. Domains may be swapped between nematicidal proteins, resulting in hybrid or chimeric toxins with improved pesticidal activity against a nematode pest or target spectrum. Methods for generating recombinant proteins and testing them for pesticidal activity against a nematode pest are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266: 17954-17958; Schnepf et al. (1990) *J. Biol. Chem.* 265: 20923-20930; Rang et al. 91999) *Appl. Environ. Microbiol.* 65:2918-2925).

In yet another embodiment, variant nucleotide and/or amino acid sequences can be obtained using one or more of error-prone PCR, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturation mutagenesis, permutational mutagenesis, synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and the like.

Vectors

A pesticidal sequence of the invention may be provided in an expression cassette for expression in a host cell of interest, e.g. a plant cell or a microbe. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Thus, further provided herein is a polypeptide comprising an amino acid sequence of the present invention that is operably linked to a heterologous leader or signal sequence.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and/or 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. In some embodiments, the nucleotide sequence is operably linked to a heterologous promoter capable of directing expression of said nucleotide sequence in a host cell, such as a microbial host cell or a plant host cell. The cassette may additionally contain at least one additional gene to be cotransformed into the organism. Alternatively, the additional gene(s) can be provided on multiple expression cassettes.

In various embodiments, the nucleotide sequence of the invention is operably linked to a heterologous promoter, e.g., a plant promoter. "Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds (1987) *Nucleic Acids Res.* 15:2343-2361. Also, the location of the promoter relative to the transcription start may be optimized. See, e.g., Roberts et al. (1979) *Proc. Natd. Acad. Sci. USA,* 76:760-764. Many suitable promoters for use in plants are well known in the art.

For instance, suitable constitutive promoters for use in plants include: the promoters from plant viruses, such as the peanut chlorotic streak caulimovirus (PClSV) promoter (U.S. Pat. No. 5,850,019); the 35S promoter from cauliflower mosaic virus (CaMV) (Odell et al. (1985) *Nature* 313:810-812); the 35S promoter described in Kay et al. (1987) Science 236: 1299-1302; promoters of *Chlorella* virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) *Plant Cell* 2:163-171 and U.S. Pat. No. 5,641,876); ubiquitin (Christensen et al. (1989) *Plant Mol. Biol.* 12:619-632 and Christensen et al. (1992) *Plant Mol. Biol.* 18:675-689) and Grefen et al. (2010) *Plant J,* 64:355-365; pEMU (Last et al. (1991) *Theor. Appl. Genet.* 81:581-588); MAS (Velten et al. (1984) *EMBO J.* 3:2723-2730 and U.S. Pat. No. 5,510,474); maize H3 histone (Lepetit et al. (1992) *Mol. Gen. Genet.* 231:276-285 and Atanassova et al. (1992) *Plant J.* 2(3):291-300); *Brassica napus* ALS3 (PCT application WO97/41228); a plant ribulose-biscarboxylase/oxygenase (RuBisCO) small subunit gene; the circovirus (AU 689 311) or the Cassava vein mosaic virus (CsVMV, U.S. Pat. No. 7,053,205); promoters from soybean (Pbdc6 or Pbdc7, described in WO/2014/150449 or ubiquitin 3 promoter described in U.S. Pat. Nos. 7,393,948 and 8,395,021); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al. (1993) PNAS 90:4567-4571); the promoter of the maize In2 gene which responds to benzenesulfonamide herbicide safeners (Hershey et al. (1991) *Mol. Gen. Genetics* 227:229-237 and Gatz et al. (1994) *Mol. Gen. Genetics* 243:32-38); and the promoter of the Tet repressor from Tn10 (Gatz et al. (1991) *Mol. Gen. Genet.* 227:229-237). Another inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. (1991) *Proc. Natl. Acad. Sci. USA* 88:10421) or the recent application of a chimeric transcription activator, XVE, for use in an estrogen receptor-based inducible plant expression system activated by estradiol (Zuo et al. (2000) *Plant J.,* 24:265-273). Other inducible promoters for use in plants are described in EP 332104, PCT WO 93/21334 and PCT WO 97/06269 which are herein incorporated by reference in their entirety. Promoters composed of portions of other promoters and partially or totally synthetic promoters can also be used. See, e.g., Ni et al. (1995) *Plant J.* 7:661-676 and PCT WO 95/14098 describing such promoters for use in plants.

In one embodiment of this invention, a promoter sequence specific for particular regions or tissues of plants can be used to express the nematicidal proteins of the invention, such as promoters specific for seeds (Datla, R. et al., 1997, Biotechnology Ann. Rev. 3, 269-296), especially the napin promoter (EP 255 378 A1), the phaseolin promoter, the glutenin promoter, the helianthinin promoter (WO92/17580), the albumin promoter (WO98/45460), the oleosin promoter (WO98/45461), the SAT1 promoter or the SAT3 promoter (PCT/US98/06978).

Use may also be made of an inducible promoter advantageously chosen from the phenylalanine ammonia lyase (PAL), HMG-CoA reductase (HMG), chitinase, glucanase, proteinase inhibitor (PI), PR1 family gene, nopaline synthase (nos) and vspB promoters (U.S. Pat. No. 5,670,349, Table 3), the HMG2 promoter (U.S. Pat. No. 5,670,349), the apple beta-galactosidase (ABG1) promoter and the apple aminocyclopropane carboxylate synthase (ACC synthase) promoter (WO98/45445). Multiple promoters can be used in the constructs of the invention, including in succession.

The promoter may include, or be modified to include, one or more enhancer elements. In some embodiments, the promoter may include a plurality of enhancer elements. Promoters containing enhancer elements provide for higher levels of transcription as compared to promoters that do not include them. Suitable enhancer elements for use in plants include the PC1SV enhancer element (U.S. Pat. No. 5,850,019), the CaMV 35S enhancer element (U.S. Pat. Nos. 5,106,739 and 5,164,316) and the FMV enhancer element (Maiti et al. (1997) *Transgenic Res.* 6:143-156); the translation activator of the tobacco mosaic virus (TMV) described in Application WO87/07644, or of the tobacco etch virus (TEV) described by Carrington & Freed 1990, J. Virol. 64: 1590-1597, for example, or introns such as the adh1 intron of maize or intron 1 of rice actin. See also PCT WO96/23898, WO2012/021794, WO2012/021797, WO2011/084370, and WO2011/028914.

Often, such constructs can contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the construct can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that, when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a polynucleotide located upstream of a coding sequence.

Other upstream or downstream untranslated elements include enhancers. Enhancers are polynucleotides that act to increase the expression of a promoter region. Enhancers are well known in the art and include, but are not limited to, the SV40 enhancer region and the 35S enhancer element.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell (synthetic DNA sequence). That is, the genes can be synthesized using host cell-preferred codons for improved expression, or may be synthesized using codons at a host-preferred codon usage frequency. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, U.S. Patent Publication No. 20090137409, and Murray et al. (1989) *Nucleic Acids Res.* 17:477-498, herein incorporated by reference.

It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Thus, in one embodiment, the nematicidal protein is targeted to the chloroplast for expression. In this manner, where the nematicidal protein is not directly inserted into the chloroplast, the expression cassette will additionally contain a nucleic acid encoding a transit peptide to direct the nematicidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the novel toxin sequences disclosed herein. In some embodiments, the protein or nucleotide sequence of the invention is advantageously combined in plants with other genes which encode proteins or RNAs that confer useful agronomic properties to such plants. Among the genes which encode proteins or RNAs that confer useful agronomic properties on the transformed plants, mention can be made of the DNA sequences encoding proteins which confer tolerance to one or more herbicides, and others which confer tolerance to certain insects, those which confer tolerance to certain diseases, DNAs that encodes RNAs that provide nematode or insect control, and the like. Such genes are in particular described in published PCT Patent Applications WO91/02071 and WO95/06128 and in U.S. Pat. No. 7,923, 602 and US Patent Application Publication No. 20100166723, each of which is herein incorporated by reference in its entirety. In various embodiments, the transgenic plant further comprises one or more additional genes for insect resistance (e.g., Cry1, such as members of the Cry1A, Cry1B, Cry1C, Cry1D, Cry1E, and Cry1F families; Cry2, such as members of the Cry2A family; Cry9, such as members of the Cry9A, Cry9B, Cry9C, Cry9D, Cry9E, and Cry9F families; etc.). It will be understood by one of skill in the art that the transgenic plant may comprise any gene imparting an agronomic trait of interest.

Among the DNA sequences encoding proteins which confer tolerance to certain herbicides on the transformed plant cells and plants, mention can be made of a bar or PAT gene or the *Streptomyces coelicolor* gene described in WO2009/152359 which confers tolerance to glufosinate herbicides, a gene encoding a suitable EPSPS which confers tolerance to herbicides having EPSPS as a target, such as glyphosate and its salts (U.S. Pat. Nos. 4,535,060, 4,769, 061, 5,094,945, 4,940,835, 5,188,642, 4,971,908, 5,145,783, 5,310,667, 5,312,910, 5,627,061, 5,633,435), a gene encoding glyphosate-n-acetyltransferase (for example, U.S. Pat. Nos. 8,222,489, 8,088,972, 8,044,261, 8,021,857, 8,008, 547, 7,999,152, 7,998,703, 7,863,503, 7,714,188, 7,709,702, 7,666,644, 7,666,643, 7,531,339, 7,527,955, and 7,405, 074), a gene encoding glyphosate oxydoreductase (for example, U.S. Pat. No. 5,463,175), or a gene encoding an HPPD inhibitor-tolerant protein (for example, the HPPD inhibitor tolerance genes described in WO 2004/055191, WO 199638567, U.S. Pat. No. 6,791,014, WO2011/068567, WO2011/076345, WO2011/085221, WO2011/094205, WO2011/068567, WO2011/094199, WO2011/094205, WO2011/145015, WO2012/056401, and WO2014/043435).

Among the DNA sequences encoding a suitable EPSPS which confer tolerance to the herbicides which have EPSPS as a target, mention will more particularly be made of the gene which encodes a plant EPSPS, in particular maize EPSPS, particularly a maize EPSPS which comprises two mutations, particularly a mutation at amino acid position 102 and a mutation at amino acid position 106 (WO2004/074443), and which is described in Patent Application U.S. Pat. No. 6,566,587, hereinafter named double mutant maize EPSPS or 2mEPSPS, or the gene which encodes an EPSPS isolated from *Agrobacterium* and which is described by sequence ID No. 2 and sequence ID No. 3 of U.S. Pat. No. 5,633,435, also named CP4.

Among the DNA sequences encoding a suitable EPSPS which confer tolerance to the herbicides which have EPSPS as a target, mention will more particularly be made of the gene which encodes an EPSPS GRG23 from *Arthrobacter globiformis*, but also the mutants GRG23 ACE1, GRG23 ACE2, or GRG23 ACE3, particularly the mutants or variants of GRG23 as described in WO2008/100353, such as GRG23 (ace3)R173K of SEQ ID No. 29 in WO2008/100353.

In the case of the DNA sequences encoding EPSPS, and more particularly encoding the above genes, the sequence encoding these enzymes is advantageously preceded by a sequence encoding a transit peptide, in particular the "optimized transit peptide" described in U.S. Pat. No. 5,510,471 or 5,633,448.

Exemplary herbicide tolerance traits that can be combined with the nucleic acid sequence of the invention further include at least one ALS (acetolactate synthase) inhibitor (WO2007/024782); a mutated *Arabidopsis* ALS/AHAS gene (U.S. Pat. No. 6,855,533); genes encoding 2,4-D-monooxygenases conferring tolerance to 2,4-D (2,4-dichlorophenoxyacetic acid) by metabolization (U.S. Pat. No. 6,153,401); and, genes encoding Dicamba monooxygenases conferring tolerance to dicamba (3,6-dichloro-2-methoxybenzoic acid) by metabolization (US 2008/0119361 and US 2008/0120739).

In various embodiments, the nucleic acid of the invention is stacked with one or more herbicide tolerant genes, including one or more HPPD inhibitor herbicide tolerant genes, and/or one or more genes tolerant to glyphosate and/or glufosinate.

Among the DNA sequences encoding proteins concerning properties of tolerance to insects, mention will more particularly be made of the Bt proteins widely described in the literature and well known to those skilled in the art. Mention will also be made of proteins extracted from bacteria such as *Photorhabdus* (WO97/17432 & WO98/08932).

Among such DNA sequences encoding proteins of interest which confer novel properties of tolerance to insects, mention will more particularly be made of the Bt Cry or VIP proteins widely described in the literature and well known to those skilled in the art. These include the Cry1F protein or hybrids derived from a Cry1F protein (e.g., the hybrid Cry1A-Cry1F proteins described in U.S. Pat. Nos. 6,326, 169; 6,281,016; 6,218,188, or toxic fragments thereof), the Cry1A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880,275) or the Cry1Ab or Bt2 protein or insecticidal fragments thereof as described in EP451878, the Cry2Ae, Cry2Af or Cry2Ag proteins as described in WO2002/057664 or toxic fragments thereof, the Cry1A.105 protein described in WO 2007/140256 (SEQ ID No. 7) or a toxic fragment thereof, the VIP3Aa19 protein of NCBI accession ABG20428, the VIP3Aa20 protein of NCBI accession ABG20429 (SEQ ID No. 2 in WO 2007/142840), the VIP3A proteins produced in the COT202 or COT203 cotton events (WO2005/054479 and WO2005/054480, respectively), the Cry proteins as described in WO2001/47952, the VIP3Aa protein or a toxic fragment thereof as described in Estruch et al. (1996), Proc Natl Acad Sci USA. 28; 93(11):5389-94 and U.S. Pat. No. 6,291,156, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932 (e.g., Waterfield et al., 2001, Appl Environ Microbiol. 67(11):5017-24; Ffrench-Constant and Bowen, 2000, Cell Mol Life Sci.; 57(5):828-33). Also any variants or mutants of any one of these proteins differing in some (1-10, preferably 1-5) amino acids from any of the above sequences, particularly the sequence of their toxic fragment, or which are fused to a transit peptide, such as a plastid transit peptide, or another protein or peptide, is included herein.

In various embodiments, the nucleic acid of the invention can be combined in plants with one or more genes conferring a desirable trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like.

Particularly useful transgenic events which may be combined with the genes of the current invention in plants of the same species (e.g., by crossing or by re-transforming a plant containing another transgenic event with a chimeric gene of the invention), include Event BPS-CV127-9 (soybean, herbicide tolerance, deposited as NCIMB No. 41603, described in WO2010/080829); Event DAS21606-3/1606 (soybean, herbicide tolerance, deposited as PTA-11028, described in WO2012/033794), Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS68416 (soybean, herbicide tolerance, deposited as ATCC PTA-10442, described in WO2011/066384 or WO2011/066360); Event DP-305423-1 (soybean, quality trait, not deposited, described in US-A 2008-312082 or WO2008/054747); Event DP-356043-5 (soybean, herbicide tolerance, deposited as ATCC PTA-8287, described in US-A 2010-0184079 or WO2008/002872); Event FG72 (soybean, herbicide tolerance, deposited as PTA-11041, described in WO2011/063413), Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON89788 (soybean, herbicide tolerance, deposited as ATCC PTA-6708, described in US-A 2006-282915 or WO2006/130436); Event SYHTOH2/SYN-000H2-5 (soybean, herbicide tolerance, deposited as PTA-11226, described in WO2012/082548), event EE-GM3/FG72 (soybean, herbicide tolerance, ATCC Accession No PTA-11041) optionally stacked with event EE-GM1/LL27 or event EE-GM2/LL55 (WO2011/063413A2); Event DAS-68416-4 (soybean, herbicide tolerance, ATCC Accession No PTA-10442, WO2011/066360A1); Event DAS-68416-4 (soybean, herbicide tolerance, ATCC Accession No PTA-10442, WO2011/066384A1); Event DAS-21606-3 (soybean, herbicide tolerance, ATCC Accession No. PTA-11028, WO2012/033794A2); Event MON-87712-4 (soybean, quality trait, ATCC Accession No. PTA-10296, WO2012/051199A2); Event DAS-44406-6 (soybean, stacked herbicide tolerance, ATCC Accession No. PTA-11336, WO2012/075426A1); Event DAS-14536-7 (soybean, stacked herbicide tolerance, ATCC Accession No. PTA-11335, WO2012/075429A1); Event SYN-000H2-5 (soybean, herbicide tolerance, ATCC Accession No. PTA-11226, WO2012/082548A2); Event 8264.44.06.1 (soybean, stacked herbicide tolerance, Accession No PTA-11336, WO2012075426A2); Event 8291.45.36.2 (soybean, stacked herbicide tolerance, Accession No. PTA-11335, WO2012075429A2); Event SYHTOH2 (soybean, ATCC Accession No. PTA-11226, WO2012/082548A2); Event pDAB8264.42.32.1 (soybean, stacked herbicide tolerance, ATCC Accession No PTA-11993, WO2013/010094A1).

Further, provided herein is a method for producing a soybean plant or seed comprising a nucleotide sequence encoding SEQ ID NO:1 or 2 combined with another SCN resistance locus/gene, such as by combining a soybean plant or seed comprising a nucleotide sequence encoding SEQ ID NO:1 or 2 with another SCN resistance locus/gene occurring in the same soybean plant/seed, and planting seed comprising a nucleotide sequence encoding SEQ ID NO:1 or 2 and said other SCN resistance locus/gene. In one embodiment, the plants, cells or seeds of the invention contain one or more other SCN resistance loci/genes that occur in soybean, to get a combination of different SCN resistance sources in the soybean plants, cells or seeds of the invention. Several soybean SCN resistance loci or genes are known and one or more of those can be combined with a plant comprising SEQ ID NO:1 or 2 in the same plant, cell or seed, such as any one of the SCN resistance genes/loci from the resistance sources PI 88788, PI 548402 (Peking), PI 437654 (Hartwig or CystX®), or any combination thereof, or one or more of the native SCN resistance loci/genes rhg1, rhg1-b, rhg2, rhg3, Rhg4, Rhg5, qSCN11, cqSCN-003, cqSCN-005, cqSCN-006, cqSCN-007, or any of the SCN resistance loci identified on any one of soybean chromosomes 1, 3, 4, 5, 6, 7, 8, 9, 10, 11, 12, 13, 14, 15, 16, 17, 18, 19, or 20 or any combination thereof (Kim et al. 2016, Theor. Appl. Genet. 129(12):2295-2311; Kim and Diers 2013, Crop Science 53:775-785; Kazi et al. 2010, Theor. Appl. Gen. 120(3):633-644; Glover et al. 2004, Crop Science 44(3):936-941; www.soybase.org; Concibido et al. 2004, Crop Science 44:1121-1131; Webb et al. 1995, Theor. Appl. Genet. 91:574-581). Also, in one embodiment the plants or seeds of the invention are combined with one or more SCN resistance loci in soybean obtained from any one of SCN resistance sources PI 548316, PI 567305, PI 437654, PI 90763, PI 404198B, PI 88788, PI 468916, PI 567516C, PI 209332, PI 438489B, PI 89772, Peking, PI 548402, PI 404198A, PI 561389B, PI 629013, PI 507471, PI 633736, PI 507354, PI 404166, PI 437655, PI 467312, PI567328, PI 22897, or PI 494182.

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*- mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, NY). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the nematicidal protein.

Pesticidal Activity in Plants

In another aspect of the invention, one may generate transgenic plants expressing a nematicidal protein that has pesticidal activity against a nematode pest. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a nematicidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity against a nematode pest.

Fertile plants expressing a nematicidal protein may be tested for pesticidal activity against a nematode pest, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Use in Pesticidal Control

General methods for employing strains comprising a nucleotide sequence of the present invention, or a variant thereof, in pest control or in engineering other organisms as pesticidal agents are known in the art. See, for example U.S. Pat. No. 5,039,523 and EP 0480762A2.

Microorganisms can be genetically altered to contain a nucleotide sequence encoding SEQ ID NO:1 or 2, or nematicidally-active variants or fragments thereof, and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of the target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the nematicidal proteins disclosed herein as SEQ ID NO:1 or 2, or nematicidally-effective variants or fragments thereof, include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Nematode pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" or "nematicidally-effective amount" is intended an amount of the pesticide or nematicide that is able to bring about death to at least one pest, or to noticeably reduce pest growth, feeding, or normal physiological development of the pest or the host plant in which the pest infests. This amount will vary depending on such factors as, for example, the specific target pests to be controlled, the specific environment, location, plant, crop, or agricultural site to be treated, the environmental conditions, and the method, rate, concentration, stability, and quantity of application of the nematicidally-effective polypeptide composition. The formulations may also vary with respect to climatic conditions, environmental considerations, and/or frequency of application and/or severity of pest infestation.

The pesticide compositions described may be made by formulating either the bacterial cell, the crystal and/or the spore suspension, or the isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

Methods for Increasing Plant Yield

Methods for increasing plant yield are provided. The methods comprise providing a plant or plant cell expressing a polynucleotide encoding the nematicidal polypeptide sequence disclosed herein and growing the plant or a seed thereof in a field infested with (or susceptible to infestation by) a nematode pest against which said polypeptide has nematicidal activity. In some embodiments, the Cry14 polypeptide described herein has nematicidal activity against a *Pratylenchus* spp., and said field is infested with said *Pratylenchus* spp. In various embodiments, the *Pratylenchus* spp. is *Pratylenchus brachyurus*. In additional embodiments, the nematode is a root knot nematode, a lesion nematode, or a Lance nematode. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal protein described herein. In specific methods, plant yield is increased as a result of improved nematode resistance of a plant expressing the nematicidal protein disclosed herein. Expression of the nematicidal protein results in a reduced ability of a pest to infest or feed. In various embodiments, expression of the nematicidal protein results in improved root development (e.g., improved root or root hair growth), improved yield, faster emergence, improved plant stress management including increased stress tolerance and/or improved recovery from stress, increased mechanical strength, improved drought resistance, reduced fungal disease infection, and improved plant health compared to a plant not expressing the nematicidal protein of the invention.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam; Fruits/Vegetables Insecticides: Aldicarb, *Bacillus* thuriengiensis, Carbaryl, Carbofuran, Chlorpyrifos, Cypermethrin, Deltamethrin, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Spirodiclofen, Gamma-cyhalothrin, Spiromesifen, Spinosad, Rynaxypyr, Cyazypyr, Triflumuron, Spirotetramat, Imidacloprid, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin-benzoate, Indoxacarb, Fenamiphos, Pyriproxifen, Fenbutatin-oxid; Fruits/Vegetables Fungicides: Ametoctradin, Azoxystrobin, Benthiavalicarb, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Fenamidone, Fenhexamid, Fluazinam, Fludioxonil, Fluopicolide, Fluopyram, Fluoxastrobin, Fluxapyroxad, Folpet, Fosetyl, Iprodione, Iprovalicarb, Isopyrazam, Kresoxim-methyl, Mancozeb, Mandipropamid, Metalaxyl/mefenoxam, Metiram, Metrafenone, Myclobutanil, Penconazole, Penthiopyrad, Picoxystrobin, Propamocarb, Propiconazole, Propineb, Proquinazid, Prothioconazole, Pyraclostrobin, Pyrimethanil, Quinoxyfen, Spiroxamine, Sulphur, Tebuconazole, Thiophanate-methyl, Trifloxystrobin; Cereals Herbicides: 2.4-D, Amidosulfuron, Bromoxynil, Carfentrazone-E, Chlorotoluron, Chlorsulfuron, Clodinafop-P, Clopyralid, Dicamba, Diclofop-M, Diflufenican, Fenoxaprop, Florasulam, Flucarbazone-NA, Flufenacet, Flupyrosulfuron-M, Fluroxypyr, Flurtamone, Glyphosate, Iodosulfuron, Ioxynil, Isoproturon, MCPA, Mesosulfuron, Metsulfuron, Pendimethalin, Pinoxaden, Propoxycarbazone, Prosulfocarb, Pyroxsulam, Sulfosulfuron, Thifensulfuron, Tralkoxydim, Triasulfuron, Tribenuron, Trifluralin, Tritosulfuron; Cereals Fungicides: Azoxystrobin, Bixafen, Boscalid, Carbendazim, Chlorothalonil, Cyflufenamid, Cyproconazole, Cyprodinil, Dimoxystrobin, Epoxiconazole, Fenpropidin, Fenpropimorph, Fluopyram, Fluoxastrobin, Fluquinconazole, Fluxapyroxad, Isopyrazam, Kresoxim-methyl, Metconazole, Metrafenone, Penthiopyrad, Picoxystrobin, Prochloraz, Propiconazole, Proquinazid, Prothioconazole, Pyraclostrobin, Quinoxyfen, Spiroxamine, Tebuconazole, Thiophanate-methyl, Trifloxystrobin; Cereals Insecticides: Dimethoate, Lambda-cyhalthrin, Deltamethrin, alpha-Cypermethrin, 3-cyfluthrin, Bifenthrin, Imidacloprid, Clothianidin, Thiamethoxam, Thiacloprid, Acetamiprid, Dinetofuran, Clorphyriphos, Pirimicarb, Methiocarb, Sulfoxaflor; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, 13-Cyfluthrin, Cypermethrin, Bifenthrin, Lufenuron, Tebupirimphos, Ethiprole, Cyazypyr, Thiacloprid, Acetamiprid, Dinetofuran, Avermectin; Maize Fungicides: Azoxystrobin, Bixafen, Boscalid, Cyproconazole, Dimoxystrobin, Epoxiconazole, Fenitropan, Fluopyram, Fluoxastrobin, Fluxapyroxad, Isopyrazam, Metconazole, Penthiopyrad, Picoxystrobin, Propiconazole, Prothioconazole, Pyraclostrobin, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenobucarb, Benfuracarb, Buprofezin, Dinotefuran, Fipronil, Imidacloprid, Isoprocarb, Thiacloprid, Chromafenozide, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Etofenprox, Carbofuran, Benfuracarb, Sulfoxaflor; Rice Fungicides: Azoxystrobin, Carbendazim, Carpropamid, Diclocymet, Difenoconazole, Edifenphos, Ferimzone, Gentamycin, Hexaconazole, Hymexazol, Iprobenfos (IBP), Isoprothiolane, Isotianil, Kasugamycin, Mancozeb, Metominostrobin, Orysastrobin, Pencycuron, Probenazole, Propiconazole, Propineb, Pyroquilon, Tebuconazole, Thiophanate-methyl, Tiadinil, Tricyclazole, Trifloxystrobin, Validamycin; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid Flubendiamide, Triflumuron,Rynaxypyr,Beta-Cyfluthrin,Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor; Cotton Fungicides: Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, 3-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Bixafen, Boscalid, Carbendazim, Chlorothalonil, Copper, Cyproconazole, Difenoconazole, Dimoxystrobin, Epoxiconazole, Fluazinam, Fluopyram, Fluoxastrobin, Flutriafol, Fluxapyroxad, Isopyrazam, Iprodione, Isotianil, Mancozeb, Maneb, Metconazole, Metominostrobin, Myclobutanil, Penthiopyrad, Picoxystrobin, Propiconazole, Propineb, Prothioconazole, Pyraclostrobin, Tebuconazole, Tetraconazole, Thiophanate-methyl, Trifloxystrobin; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, 3-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Bixafen, Boscalid, Carbendazim, Cyproconazole, Difenoconazole, Dimoxystrobin, Epoxiconazole, Fluazinam, Fluopyram, Fluoxastrobin, Flusilazole, Fluxapyroxad, Iprodione, Isopyrazam, Mepiquat-chloride, Metconazole, Metominostrobin, Paclobutrazole, Penthiopyrad., Picoxystrobin, Prochloraz, Prothioconazole, Pyraclostrobin, Tebuconazole, Thiophanate-methyl, Trifloxystrobin, Vinclozolin; Canola Insecticides: Carbofuran, Thiacloprid, Deltamethrin, Imidacloprid, Clothianidin, Thiamethoxam, Acetamiprid, Dinetofuran, 3-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

The following examples are offered by way of illustration and not by way of limitation.

EXPERIMENTAL EXAMPLES

Example 1. Cry14Aa1 Expression in Soybean

Soybean events expressing Cry14Aa1 (SEQ ID NO:3) were developed through *Agrobacterium*-mediated transformation of Thorne soybean plants using a construct containing a gene encoding a 4-hydroxyphenylpyruvate dioxygenase protein (IPPD) inhibitor tolerant herbicide gene (described in WO2014043435) and Cry14Aa1. Wild-type Thorne soybean served as the non-nematode resistant control. Cry14Aa1, when expressed in soybean plants, reduces the number of *Pratylenchus brachyurus* that reproduce in the roots compared with wild-type plants.

Three independent event lines consistently gave the same result showing nematode reduction upon retest multiple times. In all three events, the number of nematodes was reduced by 60-85%.

Example 2. Cry14Ab1 Expression in Soybean

EE-GM4 soybean events expressing Cry14Ab1 (SEQ ID NO.4) were developed through *Agrobacterium*-mediated transformation of Thorne soybean plants using a construct containing a gene encoding a 4-hydroxyphenylpyruvate dioxygenase protein (HPPD) inhibitor tolerant herbicide gene (described in WO2014043435) and Cry14Ab1. Wild-type Thorne soybean served as the non-nematode resistant control. Cry14Ab1, when expressed in soybean plants, reduces the number of *Pratylenchus brachyurus* that reproduce in the roots compared with wild-type plants. Non-transformed Thorne and EE-GM4 seeds were geminated and planted in the greenhouse to check for control of the lesion nematode, *Pratylenchus brachyurus*. *Pratylenchus brachyurus* nematodes (#1500/plant, different developmental stages) were applied to the plants when 2 weeks old. Thirty days after application, *Pratylenchus* nematodes were extracted from the roots and counted. The average number of nematodes found in the roots of plants containing EE-GM4 were compared with the average number of *Pratylenchus* nematodes found in the wild-type Thorne plant roots. On average about 80-90% fewer *Pratylenchus* nematodes were found in roots of plants containing EE-GM4 when compared with the Thorne control roots, indicating significant control of lesion nematodes by soybean event EE-GM4.

Figure 1:
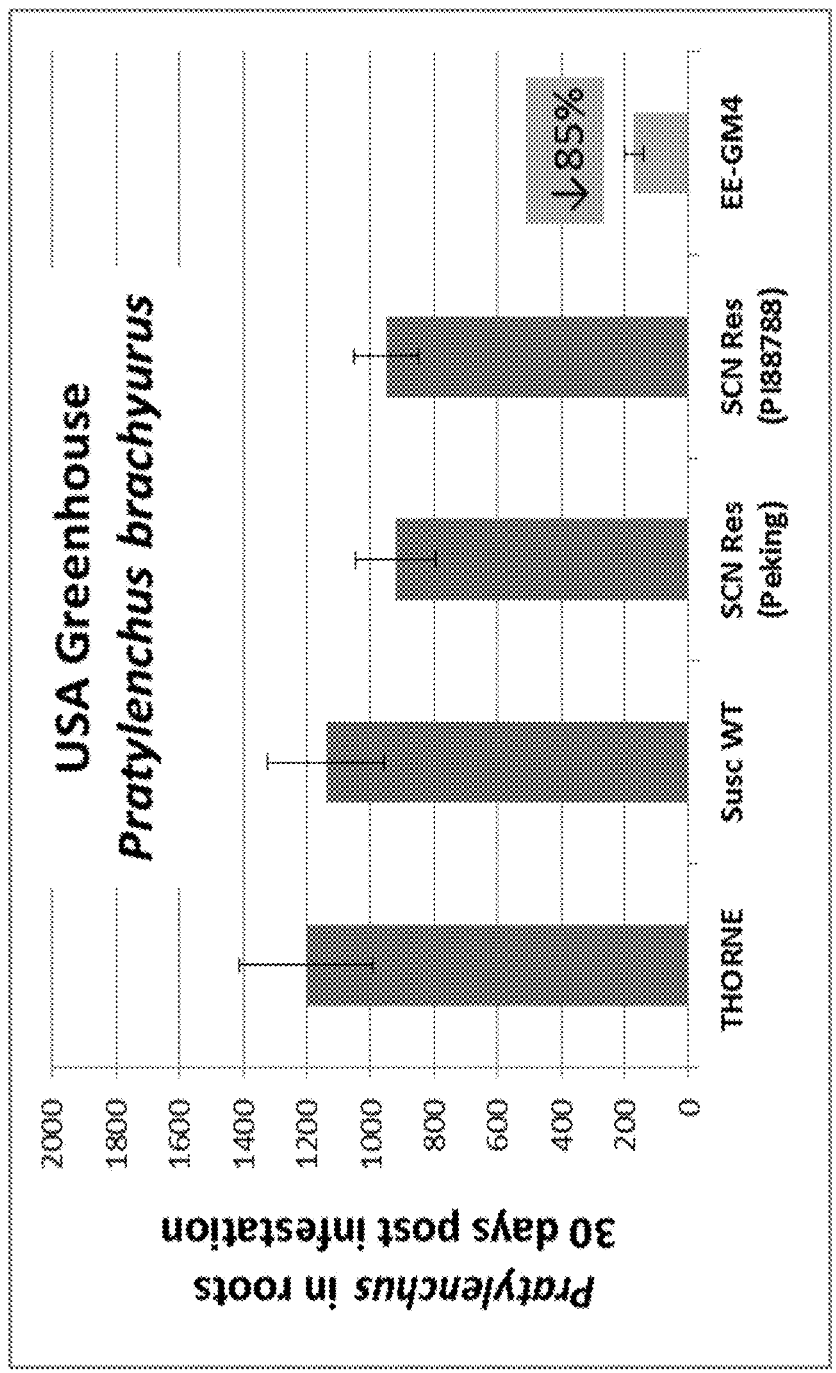
FIG. 1. *Pratylenchus* resistance greenhouse assay in the USA

FIG. 1 shows results from a *Pratylenchus brachyurus* greenhouse assay in the US, comparing elite lines with EE-GM4 in 5 elite soybean lines (one SCN susceptible (MG 1), one SCN resistant (PI88788, MG 3), one SCN susceptible (MG 6.2), one SCN resistant (Peking, MG 6.2), and one SCN susceptible (MG 9) to SCN-susceptible and SCN-resistant US soybean lines. The soybean plants were grown in small cone pots and kept in greenhouses with temperature varying between 25-32° C. *Pratylenchus brachyurus* nematodes, obtained from South Carolina and increased in the greenhouse were used to inoculate plants in the V2-V3 development stage. Approximately 1500 eggs+adults were inoculated per plant and each entry had 5 plants. Thirty days after infestation, nematodes and eggs were extracted from the roots and counted. Each entry was run in two independent experiments. While SCN-susceptible and SCN-resistant US soybean lines did not show control of *Pratylenchus*, plants with EE-GM4 showed about 85% control of *Pratylenchus*.

FIG. 2 shows results from a *Pratylenchus brachyurus* greenhouse assay in Brazil, comparing soybean plants with EE-GM4 to Brazil soybean lines with no resistance and 1 low Rf line, and SCN-susceptible and -resistant plants. The soybean lines were grown in small cone pots and kept in greenhouses with temperature varying between 25-32° C. *Pratylenchus brachyurus* nematodes, obtained from Brazil fields and increased in the greenhouse were used to inoculate plants in the V2-V3 development stage. Approximately 1000 eggs+adults were inoculated per plant and each entry had 5 plants. Thirty days after infestation, nematodes and eggs were extracted from the roots and counted. Results shown are from a single experiment. One Brazilian soybean line (BRS 7380), labeled as having a low reproductive factor for *Pratylenchus*, showed about 89% reduction of *Pratylenchus*. Plants with EE-GM4 gave ~97% control of *Pratylenchus*. Soybean lines that carry native resistance to SCN (rhg1+Rhg4) do not control *Pratylenchus brachyurus*.

Also, plants containing EE-GM4 can be used to control root-knot nematodes (RKN) such as *Meloidogyne incognita*. Even though the population of *Meloidogyne incognita* does not infest Thorne wild-type soybean very well, Thorne plants with EE-GM4 show a further reduction in the number of RKN eggs/root mass on average, as compared to untransformed Thorne plants.

Example 3. Vectoring of Genes for Plant Expression

The coding regions of the invention are connected with appropriate promoter and terminator sequences for expression in plants. Such sequences are well known in the art. Techniques for producing and confirming promoter—gene—terminator constructs also are well known in the art.

In one aspect of the invention, synthetic DNA sequences are designed and generated. These synthetic sequences have altered nucleotide sequence relative to the parent sequence, but encode proteins that are essentially identical to the parent sequence. In some embodiments, the synthetic DNA sequence comprises SEQ ID NO:3 or 4.

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENBANK® ID GI:14276838, Miller et al. (2001) Plant Physiology 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif, SEQ ID NO:7) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the amino acid sequence of the invention, as well as the KDEL (SEQ ID NO:7) sequence at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

In the present invention, an expression cassette including a synthetic gene encoding Cry14A (SEQ ID NO:1 or 2) is operably linked to the promoter region of the sucrose synthase 1 gene of *Oryza sativa* (Wang et al. (1992) Plant Molecular Biology, 19, 881-885) or the promoter region of the Cauliflower Mosaic Virus 35S transcript (Odell et al. (1985) *Nature* 313, 810-812) and the leader sequence of the chlorophyll a/b binding protein gene of *Petunia* hybrid (Harpster et al. (1988) Molecular and General Genetics 212, 182-190). The expression cassettes further comprised the 3' untranslated region of the nopaline synthase gene from the T-DNA of pTiT37 (Depicker et al. (1982) *Journal of Molecular and Applied Genetics* 1, 561-573) operably linked to the 3' end of the Cry14 sequence.

Example 4: Soybean Transformation

Soybean transformation is achieved using methods well known in the art, such as the one described using the *Agrobacterium tumefaciens* mediated transformation soybean half-seed explants using essentially the method described by Paz et al. (2006), Plant cell Rep. 25:206. Transformants are identified using tembotrione as selection marker. The appearance of green shoots was observed, and documented as an indicator of tolerance to the herbicide isoxaflutole or tembotrione. The tolerant transgenic shoots will show normal greening comparable to wild-type soybean shoots not treated with isoxaflutole or tembotrione, whereas wild-type soybean shoots treated with the same amount of isoxaflutole or tembotrione will be entirely bleached. This indicates that the presence of the HPPD protein enables the tolerance to HPPD inhibitor herbicides, like isoxaflutole or tembotrione.

Tolerant green shoots are transferred to rooting media or grafted. Rooted plantlets are transferred to the greenhouse after an acclimation period. Plants containing the transgene are then sprayed with HPPD inhibitor herbicides, as for example with tembotrione at a rate of 100 g AI/ha or with mesotrione at a rate of 300 g AI/ha supplemented with ammonium sulfate methyl ester rapeseed oil. Ten days after the application the symptoms due to the application of the herbicide are evaluated and compared to the symptoms observed on wild type plants under the same conditions.

Example 5: Cotton T0 Plant Establishment and Selection

Cotton transformation is achieved using methods well known in the art, especially preferred method in the one described in the PCT patent publication WO 00/71733. Regenerated plants are transferred to the greenhouse. Following an acclimation period, sufficiently grown plants are sprayed with HPPD inhibitor herbicides as for example tembotrione equivalent to 100 or 200 gAI/ha supplemented with ammonium sulfate and methyl ester rapeseed oil. Seven days after the spray application, the symptoms due to the treatment with the herbicide are evaluated and compared to the symptoms observed on wild type cotton plants subjected to the same treatment under the same conditions.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for controlling a *Pratylenchus brachyurus* nematode pest population comprising contacting said population with a nematicidally-effective amount of a polypeptide comprising an amino acid sequence having at least 95% sequence identity to the amino acid sequence of SEQ ID NO:1 or 2, wherein said polypeptide has nematicidal activity against the *Pratylenchus brachyurus* nematode pest population.

2. The method of claim 1, wherein said polypeptide is expressed in a soybean plant.

3. A method for protecting a plant from a *Pratylenchus brachyurus* nematode pest, comprising expressing in a plant or cell thereof a nucleotide sequence operably linked to a promoter capable of directing expression of the nucleotide sequence in a plant cell, wherein said nucleotide sequence is selected from the group consisting of:

a) the nucleotide sequence set forth in SEQ ID NO:3, the nucleotide sequence set forth in SEQ ID NO:4; and b) a nucleotide sequence that encodes a polypeptide comprising an amino acid sequence having at least 95% sequence identity to the amino acid sequence of SEQ ID NO:1, and a nucleotide sequence that encodes a polypeptide comprising an amino acid sequence having at least 95% sequence identity to the amino acid sequence of SEQ ID NO:2, wherein contact with said *Pratvlenchus brachyurus* nematode pest is made with a nematicidally-effective amount of said polypeptide.

4. A method for increasing yield in a plant comprising growing in a field a plant or a seed thereof having stably incorporated into its genome a DNA construct comprising a nucleotide sequence operably linked to a promoter capable of directing expression of the nucleotide sequence in a plant cell, wherein said nucleotide sequence is selected from the group consisting of:

a) the nucleotide sequence set forth in SEQ ID NO:3, the nucleotide sequence as set forth in SEQ ID NO:4; and b) a nucleotide sequence that encodes a polypeptide comprising an amino acid sequence having at least 95% sequence identity to the amino acid sequence of SEQ ID NO:1, and a nucleotide sequence that encodes a polypeptide comprising an amino acid sequence having at least 95% sequence identity to the amino acid sequence of SEQ ID NO:2, wherein contact with *Pratvlenchus brachyurus* nematode pest is made with a nematicidally-effective amount of said polypeptide; and wherein said field is infested with the *Pratylenchus brachyurus* nematode pest.

5. The method of claim 3, wherein said plant further comprises one or more nucleotide sequences encoding one or more insect toxins.

* * * * *